United States Patent [19]

Bird et al.

[11] Patent Number: 4,517,202
[45] Date of Patent: May 14, 1985

[54] PROSTAGLANDIN ANALOGUES

[75] Inventors: Clive W. Bird, Upminster; Helene I. Butler, Blandford; Michael P. L. Caton; Edward C. J. Coffee, both of Upminster; Geoffrey Darnbrough, Maldon; Terance W. Hart, Brentwood, all of England

[73] Assignee: May & Baker Limited, Essex, England

[21] Appl. No.: 498,315

[22] Filed: May 26, 1983

[30] Foreign Application Priority Data

May 28, 1982 [GB] United Kingdom ............... 8215742

[51] Int. Cl.³ .................. C07C 177/00; A61K 31/557
[52] U.S. Cl. ...................................... 514/530; 536/46; 560/51; 560/53; 560/56; 560/116; 560/119; 562/460; 562/462; 562/498; 562/501; 514/573
[58] Field of Search .............. 560/119, 498, 462, 460; 562/501, 51, 53, 56, 116; 424/305, 308, 317; 536/46

[56] References Cited

U.S. PATENT DOCUMENTS 4,192,891 3/1980 Haslanger ........................... 424/305

Primary Examiner—Robert Gerstl
Attorney, Agent, or Firm—Stevens, Davis, Miller & Mosher

[57] ABSTRACT

Prostaglandin analogues of the general formula:

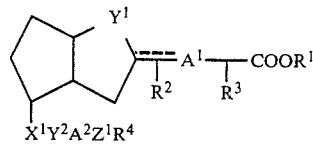

(wherein $R^1$ represents a hydrogen atom or a straight- or branched-chain alkyl group, $Y^1$ represents a carbonyl or hydroxymethylene group, ==== represents a single or double bond, $A^1$ represents an alkylene linkage containing 2 or 3 carbon atoms and optionally bearing a methyl or ethyl substituent, $R^2$ represents a hydrogen atom or a methyl or ethyl group and $R^3$ represents a hydrogen atom or else $R^2$ and $R^3$ form an alkylene linkage containing 2 or 3 carbon atoms, optionally bearing a methyl or ethyl substituent, such that the symbols $A^1$, $R^2$ and $R^3$, together with the carbon atoms through which they are connected, form a cycloalkyl ring of 6, 7 or 8 carbon atoms, optionally bearing one or two methyl or ethyl substituents, $X^1$ represents an ethylene or trans-vinylene group, $Y^2$ represents a carbonyl or hydroxymethylene group, and either (i) $A^2$ represents a straight- or branched-alkylene chain containing from 1 to 3 carbon atoms, $Z^1$ represents a direct bond or an oxygen or sulphur atom, and $R^4$ represents a straight- or branched-chain alkyl group containing from 1 to 12 carbon atoms, optionally substituted by a cycloalkyl group containing from 3 to 8 carbon atoms, or represents a cycloalkyl group containing from 3 to 8 carbon atoms, or represents a phenyl group optionally substituted by a halogen atom or by a trifluoromethyl group or by a straight- or branched-chain alkyl or alkoxy group containing from 1 to 6 carbon atoms, or (ii) $A^2$ and $Z^1$ both represent direct bonds and $R^4$ represents a straight- or branched-chain alkyl group containing from 1 to 12 carbon atoms, optionally substituted by a cycloalkyl group containing from 3 to 8 carbon atoms, or represents a cycloalkyl group containing from 3 to 8 carbon atoms) and cyclodextrin clathrates thereof and, when $R^1$ represents a hydrogen atom, non-toxic salts thereof, possess useful pharmacological properties.

21 Claims, No Drawings

PROSTAGLANDIN ANALOGUES

DESCRIPTION

This invention relates to new prostaglandin I$_2$ analogues, to processes for their preparation, to pharmaceutical compositions containing them, and to key intermediates which can be used in their preparation.

Prostaglandin I$_2$ (otherwise known as PGI$_2$ or prostacyclin) is a physiologically active natural substance having the formula shown in FIG. I of the drawings assembled at the end of this specification and its chemical name is (5Z,13E)-(9S,11R,15S)-6,9-epoxy-11,15-dihydroxyprosta-5,13-dienoic acid [Nature, 263, 663 (1976), Prostaglandins, 12, 685 (1976), ibid, 12, 915 (1976), ibid, 13, 3 (1977), ibid, 13, 375 (1977) and Chemical and Engineering News, Dec. 20, 17 (1976)].

It is well known that PGI$_2$ can be prepared by incubation of prostaglandin G$_2$ (PGG$_2$) or prostaglandin H$_2$ (PGH$_2$) with microsomal fractions prepared from thoracic aorta of swine, mesenteric artery of swine, rabbit aorta or the stomach fundus of rats. PGI$_2$ has a strong relaxing activity on the artery and some other kinds of smooth muscle. Furthermore, PGI$_2$ strongly inhibits arachidonic acid-induced blood platelet aggregation of the human.

Taking into consideration that thromboxane A$_2$, prepared by incubation of PGG$_2$ or PGH$_2$ with blood platelet microsome, has a contracting activity on the artery and an aggregating activity on blood platelets, the properties of PGI$_2$ heretofore mentioned show that PGI$_2$ fulfils a very important physiological part in a living body. PGI$_2$ may be useful in the treatment of arteriosclerosis, atherosclerosis, cardiac failure, thrombosis, hypertension, angina or asthma.

Natural PGI$_2$ is so unstable (being deactivated in a buffer solution at pH 7.6 after 20 minutes at 22° C., or after 10 minutes at 37° C.) that application of PGI$_2$ for medical purposes is difficult.

Widespread investigations have been carried out in order to discover processes for the chemical preparation of more stable analogues of PGI$_2$, and their products possessing the pharmacological properties of the 'natural' PGI$_2$ or one or more of such properties to an enhanced degree, or hitherto unknown pharmacological properties. As a result of extensive research and experimentation it has been discovered that in certain analogues of PGI$_2$ and derivatives thereof the properties of the 'natural' PGI$_2$ are, in some aspects of its activities, improved or modified.

The present invention accordingly provides new prostaglandin analogues of the general formula shown in FIG. II [wherein $R^1$ represents a hydrogen atom or a straight- or branched-chain alkyl group preferably containing from 1 to 6 carbon atoms, $Y^1$ represents a carbonyl or hydroxymethylene group, ===== represents a single or double bond, $A^1$ represents an alkylene linkage containing 2 or 3 carbon atoms and optionally bearing a methyl or ethyl substituent, $R^2$ represents a hydrogen atom or a methyl or ethyl group and $R^3$ represents a hydrogen atom or else $R^2$ and $R^3$ form an alkylene linkage containing 2 or 3 carbon atoms, optionally bearing a methyl or ethyl substituent, such that the symbols $A^1$, $R^2$ and $R^3$, together with the carbon atoms through which they are connected, form a cycloalkyl ring of 6, 7 or 8 carbon atoms, optionally bearing one or two methyl or ethyl substituents, $X^1$ represents an ethylene or trans-vinylene group, $Y^2$ represents a carbonyl or hydroxymethylene group, and either (i) $A^2$ represents a straight- or branched-alkylene chain containing from 1 to 3 carbon atoms, $Z^1$ represents a direct bond or an oxygen or sulphur atom, and $R^4$ represents a straight- or branched-chain alkyl group containing from 1 to 12 carbon atoms, optionally substituted by a cycloalkyl group containing from 3 to 8 carbon atoms, or represents a cycloalkyl group containing from 3 to 8 carbon atoms, or represents a phenyl group optionally substituted by a halogen (e.g. chlorine, bromine, fluorine or iodine) atom or by a trifluoromethyl group or by a straight- or branched-chain alkyl or alkoxy group containing from 1 to 6 carbon atoms, or (ii) $A^2$ and $Z^1$ both represent direct bonds and $R^4$ represents a straight- or branched-chain alkyl group containing from 1 to 12 carbon atoms, optionally substituted by a cycloalkyl group containing from 3 to 8 carbon atoms, or represents a cycloalkyl group containing from 3 to 8 carbon atoms] as well as the cyclodextrin clathrates and, when $R^1$ represents a hydrogen atom, non-toxic salts thereof.

In this specification, whenever reference is made to compounds of the formula shown in FIG. II, it is intended to refer also to the said cyclodextrin clathrates and non-toxic salts thereof whenever the context so permits.

As will be apparent to those skilled in the art, the compounds of the formula shown in FIG. II have at least three centres of chirality, these three centres of chirality being at the carbon atoms in positions 8, 9 and 12. In addition to these three centres of chirality, a further centre of chirality will occur when $Y^1$ or $Y^2$ represents a hydroxymethylene group and still further centres of chirality may occur in the groups $A^1$, $R^1$ and $R^2$ and in positions 2, 5 and 6. The presence of centres of chirality, as is well known, leads to the existence of isomerism. However, the compounds of the formula shown in FIG. II all have such a configuration that the hydrogen atoms attached to the bridgehead carbon atom in positions 8 and 9 are cis with respect to each other. Accordingly, all isomers of the formula shown in FIG. II, and mixtures thereof, which have those hydrogen atoms, attached to the bridgehead carbon atoms in positions 8 and 9, in the cis-configuration are within the scope of the present invention. Preferably the hydrogen atoms attached to the 8 and 9 positions are in the same configurations as those in PGI$_2$, viz. beta and beta respectively. Particularly preferred compounds are those wherein the sidechain attached in the 12-position is cis with respect to the said hydrogen atoms attached to the bridgehead carbon atoms in positions 8 and 9.

Those skilled in the art will also appreciate that ===== can be in the (E) or the (Z)-configuration when it represents a vinylene group.

According to a feature of the present invention compounds of the formula shown in FIG. II in the (5Z)-configuration can be prepared by the irradiation of corresponding compounds of the formula shown in FIG. II in the (5E)-configuration. Usually ultra-violet radiation is used, and it is convenient to use the 254 nm rays emitted by a low pressure mercury vapour lamp.

Compounds of the formula shown in FIG. II which are of especial importance are those of the general formula shown in FIG. III (wherein $A^1$, $A^2$, $R^1$, $R^2$, $R^3$, $R^4$, =====, $X^1$, $Y^1$, $Y^2$ and $Z^1$ are as hereinbefore defined) and also their enantiomers and non-toxic salts and cyclodextrin clathrates thereof.

Especially preferred classes of compounds of the formula shown in FIG. II are those which exhibit one or more of the following features:

(i) A¹ represents an ethylene group;
(ii) A² represents a direct bond or a methylene group;
(iii) R⁴ represents a straight- or branched-chain alkyl group containing from 1 to 12, preferably from 4 to 8, carbon atoms, more especially a pentyl group, or represents a cycloalkyl group containing from 3 to 8 carbon atoms, more especially a cyclohexyl group, or a phenyl group;
(iv) R¹ represents a hydrogen atom or a methyl or ethyl group;
(v) R² represents a hydrogen atom or a methyl group;
(vi) R³ represents a hydrogen atom;
(vii) A¹, R² and R³, together with the carbon atoms through which they are connected, form a cyclohexyl ring;
(viii) ===== represents a vinylene group;
(ix) X¹ represents a trans-vinylene group;
(x) Y² represents a hydroxymethylene group;
(xi) Z¹ represents a direct bond or an oxygen atom;

Individual compounds of particular importance include the following:

| | |
|---|---|
| (±)-methyl (5E,13E)-(9S,15S)-6a-oxo-6,9-methano-15-cyclohexyl-15-hydroxy-16,17,18,19,20-pentanorprosta-5,13-dienoate; | A |
| (±)-(5E,13E)-(9S,15S)-6a-oxo-6,9-methano-15-cyclohexyl-15-hydroxy-16,17,18,19,20-pentanorprosta-5,13-dienoic acid; | B |
| (±)-[mixture of (5E) and (5Z)], (13E)-(9S,15S)-6a-oxo-6,9-methano-15-cyclohexyl-15-hydroxy-16,17,18,19,20-pentanorprosta-5,13-dienoic acid; | C |
| (±)-methyl (5E,13E)-(9S), [mixture of (15R) and (15S)]-6a-oxo-6,9-methano-15-hydroxyprosta-5,13-dienoate; | D |
| (±)-(5E,13E)-(9S), [mixture of (15R) and (15S)]-6a-oxo-6,9-methano-15-hydroxyprosta-5,13-dienoic acid; | E |
| (±)-(5Z,13E)-(9S), [mixture of (15R) and (15S)]-6a-oxo-6,9-methano-15-hydroxyprosta-5,13-dienoic acid; | F |
| (±)-methyl (5Z,.13E)-(9S), [mixture of (15R) and (15S)]-6a-oxo-6,9-methano-15-hydroxyprosta-5,13-dienoate; | G |
| (±)-methyl (5E,13E)-(9S), [mixture of (15R) and (15S)]-6a-oxo-6,9-methano-15-cyclohexyl-15-hydroxy-16,17,18,19,20-pentanorprosta-5,13-dienoate; | H |
| (±)-(5E,13E)-(9S), [mixture of (15R) and (15S)]-6a-oxo-6,9-methano-15-cyclohexyl-15-hydroxy-16,17,18,19,20-pentanorprosta-5,13-dienoic acid; | I |
| (±)-(5E,13E)-(6aS,9S), [mixture of (15R) and (15S)]-6a,15-dihydroxy-6,9-methano-15-cyclohexyl-16,17,18,19,20-pentanorprosta-5,13-dienoic acid; | J |
| (±)-ethyl (13E)-(9S,15S)-6a-oxo-2,5-ethano-6,9-methano-15-hydroxy-15-cyclohexyl-16,17,18,19,20-pentanorprosta-5,13-dienoate; | K |
| (±)-methyl (5E,13E)-(9S,15R)-6a-oxo-6,9-methano-15-cyclohexyl-15-hydroxy-16,17,18,19,20-pentanorprosta-5,13-dienoate; | L |
| (±)-(5E,13E)-(9S,15R)-6a-oxo-6,9-methano-15-cyclohexyl-15-hydroxy-16,17,18,19,20-pentanorprosta-5,13-dienoic acid; | M |
| (±)-ethyl [mixture of (5E) and (5Z)], (13E)-(9S,15R)-6a-oxo-6,9-methano-5-methyl-15-cyclohexyl-15-hydroxy-16,17,18,19,20 pentanorprosta-5,13-dienoate; | N |
| (±)-ethyl (13E)-(9S,15R)-6a-oxo-2,5-ethano-6,9-methano-15-hydroxy-15-cyclohexyl-16,17,18,19,20-pentanorprosta-5,13-dienoate; | O |
| (±)-methyl (5E,13E)-(9S,15S)-6a-oxo-6,9-methano-15-hydroxy-16-phenoxy-17,18,19,20-tetranorprosta-5,13-dienoate; | P |
| (±)-methyl (5E,13E)-(9S,15R)-6a-oxo-6,9-methano-15-hydroxy-16-phenoxy-17,18,19,20-tetranorprosta-5,13-dienoate; and | Q |
| (±)-methyl (5E,13E)-(9S), [mixture of (15R) and (15S)]-6a-oxo-6,9-methano-15-hydroxy-16-phenoxy-17,18,19,20-tetranorprosta-5,13-dienoate. | R |

The letters A to R are assigned to the compounds for easy reference later in the specification.

The compounds of the formula shown in FIG. II and cyclodextrin clathrates and non-toxic salts thereof possess valuable pharmacological properties, for example, properties typical of the related series of natural products known as prostaglandins.

In laboratory screening tests the compounds produced in inhibition of collagen-induced β-thromboglobulin release in vitro in human blood, as shown in Table I below, which indicates the concentrations of the test compounds (ED₅₀) in μg/ml which produced 50% inhibition of the β-thromboglobulin release.

In other laboratory tests, compound B produced a 25% fall in diastolic blood pressure in rats (anaesthetised with pentobarbitone) when administered intravenously at a rate of 45 μg/kg animal body weight.

These results are indicative of utility in the prevention or treatment of conditions such as hypertension, thrombosis, and possibly arteriosclerosis, atherosclerosis, and cardiac conditions such as angina and myocardial infarction.

This utility is enhanced by the fact that the compounds of the formula shown in FIG. II are far more stable than natural PGI₂ and so they and their pharmaceutical compositions may be manipulated, stored and administered relatively easily.

TABLE I

| Test Compound | ED₅₀ μg/ml |
|---|---|
| B | 5 |
| E | 34 |
| F | less than 17 |
| I | less than 17 |

According to a feature of the present invention, compounds of the formula shown in FIG. II wherein Y² represents a hydroxymethylene group are prepared by the acid hydrolysis of compounds of the general formula shown in FIG. IV wherein A¹, A², R¹, R², R³, R⁴, =====, X¹, Y¹ and Z¹ are as hereinbefore defined and R⁵ represents a suitable acid-labile protecting group.

This process is particularly applicable to the preparation of compounds of the formula shown in FIG. II wherein R¹ represents an alkyl group, ===== represents a vinylene group, X¹ represents a trans-vinylene group, Y¹ represents a carbonyl group, and Y² represents a hydroxymethylene group, that is to say the preparation of compounds of the general formula shown in FIG. V (wherein A¹, A², R², R³, R⁴ and Z¹ are as hereinbefore defined and R⁶ represents a straight- or branched-chain alkyl group preferably containing from 1 to 6 carbon atoms) by the acid hydrolysis of compounds of the general formula shown in FIG. VI (wherein A¹, A², R², R³, R⁴, R⁵, R⁶ and Z¹ are as hereinbefore defined), within the formula shown in FIG. IV.

Hydrolysis of compounds of the formula shown in FIG. IV is generally effected in mild acidic conditions, for example by treatment with an aqueous inorganic acid, e.g. dilute hydrochloric acid or a catalytic quantity of perchloric acid, or an aqueous organic acid, for example aqueous acetic acid, e.g. 50–80% v/v aqueous acetic acid, preferably in the presence of an inert organic solvent, for example a lower alkanol, e.g. ethanol, or an ether, e.g. diethyl ether or tetrahydrofuran, and optionally in the presence of a cation exchange resin, e.g. Dowex $AG_{50}W$-X8 H+ resin. The hydrolysis is generally carried out at temperatures from 0° C. to 100° C.; when dilute hydrochloric acid is used, at from 40° to 80° C., preferably from 50° to 60° C.; when a catalytic quantity of perchloric acid is used, at from 0° to 40° C., preferably from 15° to 25° C.; and when aqueous acetic acid is used, at from 0° to 80° C., preferably from 35° to 50° C.

Suitable acid labile protecting groups represented by $R^5$ are those which are easily removed by acid hydrolysis and which do not cause side reactions, e.g. a 2-tetrahydropyranyl group unsubstituted or substituted by at least one straight- or branched-chain alkyl group containing from 1 to 4 carbon atoms, or a 2-tetrahydrofuranyl group, or a tert-butyldiphenylsilyl group, or a trialkylsilyl group of the general formula:

$$-SiR^7R^8R^9 \qquad \text{VII}$$

(wherein $R^8$ and $R^9$, which may be the same or different, each represents a methyl or ethyl group and $R^7$ represents a straight- or branched-chain alkyl group containing from 1 to 4 carbon atoms), e.g. a trimethylsilyl, triethyl, dimethylisopropylsilyl or tert-butyldimethylsilyl group, or a 1-alkoxyalkyl group of the general formula:

$$-CH(CH_2R^{10})OR^{11} \qquad \text{VIII}$$

(wherein $R^{10}$ represents a hydrogen atom or a straight- or branched-chain alkyl group containing from 1 to 4 carbon atoms and $R^{11}$ represents a straight- or branched-chain alkyl group containing from 1 to 4 carbon atoms) e.g. a 1-ethoxyethyl group.

Preferably $R^5$ represents a tert-butyldimethylsilyl group.

Compounds of the formula shown in FIG. II may be prepared from other compounds of the formula shown in FIG. II. Thus, according to a further feature of the present invention, the compounds of the formula shown in FIG. V are converted to compounds of the formula shown in FIG. II, wherein $A^1$, $A^2$, $R^1$, $R^2$, $R^3$, $R^4$, , $X^1$, $Y^1$, $Y^2$ and $Z^1$ are as hereinbefore defined but wherein one or more of the symbols $R^1$, , $X^1$, $Y^1$ and $Y^2$ have the following significances:

(a) $R^1$ represents a hydrogen atom;
(b)  represents an ethylene group;
(c) $X^1$ represents an ethylene group;
(d) $Y^1$ represents a hydroxymethylene group;
(e) $Y^2$ represents a carbonyl group;

or to salts of compounds of the formula shown in FIG. II wherein $R^1$ represents a hydrogen atom, or to cyclodextrin clathrates of the compounds of the formula shown in FIG. II, by the application or adaptation of one or more known methods of preparing acids from esters, of preparing alcohols from ketones, of preparing ketones from alcohols, of reducing carbon-carbon double bonds, of preparing salts from acids, or of preparing cyclodextrin clathrates. Furthermore, esters of the formula shown in FIG. II wherein $R^1$ represents an alkyl group can be prepared by the esterification of corresponding carboxylic acids of the formula shown in FIG. II wherein $R^1$ represents a hydrogen atom.

Thus, (1) compounds of the formula shown in FIG. II in which $R^1$ represents a hydrogen atom may be prepared by the hydrolysis of the corresponding compounds of the formula shown in FIG. II wherein $R^1$ represents an alkyl group by hydrolysis, for example with an aqueous alkali (e.g. lithium hydroxide, sodium hydroxide or potassium hydroxide), followed by treatment with dilute acid, e.g. hydrochloric acid, to generate the desired carboxylic acid product from the solution of alkali metal salt produced thereby.

(2) Compounds of the formula shown in FIG. II wherein 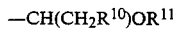, $X^1$, $Y^1$ and $Y^2$ do not simultaneously represent two vinylene groups and two carbonyl groups respectively (hereinafter referred to as "compounds of formula IIa") are prepared by the reduction of compounds of the formula shown in FIG. II wherein 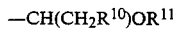, $X^1$, $Y^1$ and $Y^2$ do not simultaneously represent two ethylene groups and two hydroxymethylene groups respectively (hereinafter referred to as "compounds of formula IIb"). Thus:

(2) (a) Compouhnds of formula IIa wherein 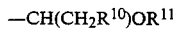 and $X^1$ represent ethylene or vinylene groups and one or both of $Y^1$ and $Y^2$ represents a hydroxymethylene group are prepared by reduction of the corresponding compounds of formula IIb wherein 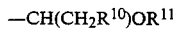 and $X^1$ each represents an ethylene or vinylene group and one or both of $Y^1$ or $Y^2$ represents carbonyl, using means and conditions capable of reducing carbonyl groups to hydroxymethylene groups without affecting carbon-carbon double bonds. The reduction is preferably effected by a metal borohydride or a metal alkylborohydride (e.g. sodium borohydride or potassium borohydride or lithium tri-sec-butylborohydride), usually in an aqueous, alcoholic or aqueous alcoholic medium and at between −40° and +30° C., preferably between −5° and +15° C., optionally in the presence of a base, for example an alkali metal hydroxide (e.g. aqueous sodium hydroxide or aqueous potassium hydroxide) when a metal borohydride is employed or, especially when potassium borohydride is employed, in aqueous or aqueous alcoholic conditions buffered at a pH of from pH 7 to pH 9, e.g. at pH 8 (e.g. by the addition of aqueous citric acid solution), or, when a metal alkylborohydride is employed, in an ethereal medium (e.g. tetrahydrofuran) at between −78° and 0° C.

Alternatively the reduction is carried out by reaction with aluminium isopropoxide, in the presence of isopropanol, preferably as the solvent medium, at an elevated temperature, advantageously at the reflux temperature of the reaction mixture.

(2) (b) Compounds of formula IIa wherein one or both of 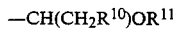 and $X^1$ represents an ethylene group and $Y^1$ and $Y^2$ each represents a carbonyl or hydroxymethylene group are prepared by reduction of the corresponding compounds of formula IIb wherein one or both of 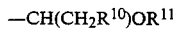 and $X^1$ represents a vinylene group and $Y^1$ and $Y^2$ each represents a carbonyl or hydroxymethylene group, with means and in conditions capable of reducing carbon-carbon double bonds without affecting carbonyl groups. The reduction is preferably effected by hydrogenation in the presence of a hydrogenation catalyst, for example rhodium on charcoal, in the presence of an inert organic solvent, for example a lower alkanol, e.g. ethanol, generally at ambient temperature and elevated pressure, e.g. at a hydrogen pressure of 15 kilograms per square centimeter.

(2) (c) Compounds of formula IIa wherein 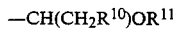 and $X^1$ both represent ethylene groups and $Y^1$ and $Y^2$ both represent hydroxy-methylene groups are prepared by reduction of corresponding compounds of formula IIb with means and in conditions capable of reducing any carbonyl groups represent to hydroxymethylene groups and any vinylene groups present to ethylene groups. In reduction is preferably effected by hydrogenation in the presence of a hydrogenation catalyst, for example palladium on charcoal, in the presence of an inert organic solvent, for example a lower alkanol, e.g. ethanol, preferably at an elevated pressure, e.g. at a hydrogen pressure of 15 kilograms per square centimeter.

(3) Compounds of the formula shown in FIG. II wherein one or both of $Y^1$ and $Y^2$ represents a carbonyl group may be prepared by oxidation of the corresponding compounds of the formula shown in FIG. II wherein one or both of $Y^1$ and $Y^2$ represents a hydroxymethylene group with means and in conditions capable of oxidising hydroxymethylene groups to form carbonyl groups without affecting the rest of the molecule. The oxidation is preferably effected by means of pyridinium chlorochromate, preferably in dichloromethane, or by means of pyridinium dichromate, preferably in dimethylformamide or dichloromethane, at or near room temperature, or by means of a solution prepared from chromium trioxide, sulphuric acid and water, preferably in the presence of acetone and at or below room temperature.

(4) By the term "non-toxic salts" is meant salts the cations of which are relatively innocuous to the animal organism when used in therapeutic doses so that the beneficial properties of the parent compound of the formula shown in FIG. II are not vitiated by side-effects ascribable to those cations. Preferably, the salts are water-soluble. Suitable salts include the alkali metal, e.g. sodium or potassium, and ammonium salts and pharmaceutically-acceptable (i.e. non-toxic) amine salts.

Amines suitable for forming such salts with carboxylic acids are well known and include, for example, amines derived in theory by the replacement of one or more of the hydrogen atoms of ammonia by groups, which may be the same or different when more than one hydrogen atom is replaced, selected from alkyl groups containing from 1 to 6 carbon atoms, hydroxyalkyl groups containing 2 or 3 carbon atoms, cycloalkyl groups containing from 3 to 6 carbon atoms, phenyl groups, phenylalkyl groups containing from 7 to 11 carbon atoms and phenylalkyl groups containing from 7 to 15 carbon atoms wherein the alkyl moieties are substituted by hydroxy groups. The phenyl groups and phenyl moieties of such phenylalkyl groups may be unsubstituted or substituted by one or two alkyl groups containing from 1 to 6 carbon atoms. Suitable amines also include those derived in theory by the replacement of two of the hydrogen atoms of ammonia by a hydrocarbon chain, which may be interrupted by nitrogen, oxygen or sulphur atoms, to form, together with the nitrogen atom of ammonia to which its terminal groups are attached, a five- or six-membered nitrogen-containing heterocyclic ring, which heterocyclic ring may be unsubstituted or substituted by one or two alkyl groups containing from 1 to 6 carbon atoms. Examples of suitable amine cations include mono-, di- and tri-methylammonium, mono-, di- and tri-ethylammonium, mono-, di- and tri-propylammonium, mono-, di- and tri-isopropylammonium, ethyldimethylammonium, mono-, bis- and tris-(2-hydroxyethyl)ammonium, ethylbis(2-hydroxyethyl)ammonium, butylmono-(2-hydroxyethyl)ammonium, tris(hydroxymethyl)methylammonium, cyclohexylammonium, benzylammonium, benzyldimethylammonium, dibenzylammonium, phenyl-2-hydroxyethylammonium, piperidinium, morpholinium, pyrrolidinium, piperazinium, 1-methylpiperidinium, 4-ethylmorpholinium, 1-isopropylpyrrolidinium, 1,4-dimethylpiperazinium, 1-butylpiperidinium, 2-methylpiperidinium and 1-ethyl-2-methylpiperidinium.

The non-toxic salts may be prepared from parent compounds of the formula shown in FIG. II by known methods, for example by reaction of stoichiometric quantities of compounds of the formula shown in FIG. II (wherein $R^1$ represents a hydrogen atom) and the appropriate base, e.g. an alkali metal hydroxide or carbonate, ammonia or an amine, in a suitable solvent which is preferably water in the case of the preparation of alkali metal salts and water or ispropanol in the case of amine salts. The salts may be isolated by lyophilisation of the solution or, if sufficiently insoluble in the reaction medium, by filtration, if necessary after removal of part of the solvent.

As well as being useful in themselves as pharmaceutically useful compounds, salts of the compounds of the formula shown in FIG. II wherein $R^1$ represents a hydrogen atom are useful for the purpose of purification of the parent acids of the formula shown in FIG. II, for example by exploitation of the solubility differences between the salts and the parent acids in water and in organic solvents, by techniques well known to those skilled in the art. The parent acids of the formula shown in FIG. II can be regenerated from their salts by known methods, for example by treatment with a mineral acid, e.g. dilute hydrochloric acid.

(5) Cyclodextrin clathrates of the prostaglandin analogues of the formula shown in FIG. II may be prepared by dissolving the cyclodextrin in water or an organic solvent which is miscible with water, in the presence of triethylamine, and adding to the solution the prostaglandin analogue in a water-miscible organic solvent. The mixture is then heated and the desired cyclodextrin clathrate product isolated by concentrating the mixture under reduced pressure or by cooling and separating the product by filtration or decantation. The ratio of organic solvent to water may be varied according to the solubilities of the starting materials and products. Preferably the temperature is not allowed to exceed 70° C. during the preparation of the cyclodextrin clathrates. α-, β- or γ-Cyclodextrins or mixtures thereof may be used in the preparation of the cyclodextrin clathrates. Conversion into their cyclodextrin clathrates serves to increase the stability of the prostaglandin analogues.

(6) Compounds of the formula shown in FIG. II wherein $R^1$ represents an alkyl group may be prepared by the reaction of a corresponding carboxylic acid of the formula shown in FIG. II in which $R^1$ represents a hydrogen atom with an alcohol of the general formula:

$$R^6OH \qquad \qquad IX$$

(wherein $R^6$ is as hereinbefore defined), an excess of which may be employed as solvent medium, in the presence of an inorganic acid, e.g. hydrochloric acid or sulphuric acid, preferably at a temperature between 50° and 160° C., and advantageously at the reflux temperature of the reaction mixture, or, where $R^6$ can be represented by the formula —$CHR^{12}R^{13}$ [wherein the symbols $R^{12}$ and $R^{13}$ are identical or different and each represents an alkyl group (the total number of carbon atoms in the two groups $R^{12}$ and $R^{13}$ being preferably at most 11) or, preferably, a hydrogen atom], with a diazoalkane of the general formula:

$$R^{12}R^{13}C=N_2 \qquad X$$

(wherein $R^{12}$ and $R^{13}$ are as hereinbefore defined) in an inert organic solvent medium, preferably a dialkyl ether (e.g. diethyl ether), preferably at ambient temperature. Alternatively, a silver salt of such as carboxylic acid of the formula shown in FIG. II can be reacted with an alkyl halide of the general formula:

$$R^6Z^2 \qquad XI$$

wherein $Z^2$ represents a halogen atom and $R^6$ is as hereinbefore defined, optionally in the presence of an inert organic solvent such as an aromatic hydrocarbon (e.g. benzene) at an elevated temperature and advantageously at the reflux temperature of the reaction mixture, or a sodium salt of a said carboxylic acid of the formula shown in FIG. II can be reacted with a said alkyl halide in a polar solvent, such as hexamethylphosphotriamide, preferably at room temperature.

By the term "known methods" as used in this specification is meant methods heretofore used or described in the literature.

As will be readily appreciated by those skilled in the art, the compounds of the formula shown in FIG. II, including their isomers arising from the aforementioned centres of chirality, may be separated by the application or adaptation of known methods, For example, diastereoisomeric forms may be separated by chromatography using selective adsorption from solution or from the vapour phase onto suitable adsorbents, and enantiomeric forms of compounds of the formula shown in FIG. II wherein $R^1$ represents a hydrogen atom may be separated by formation of salts with an optically active base, followed by separation of the obtained pair of diastereoisomers by, for example, fractional crystallisation from a suitable solvent system, followed by separate regeneration of the enantiomeric acids.

Compounds of the formula shown in FIG. IV may be prepared by the application or adaptation of known methods, for example methods illustrated in the description in the following Reference Examples for the preparation of compounds of the formula shown in FIG. VI.

An essential feature of any such multistage process for the preparation of compounds of the formula shown in FIG. II is the formation of the bicyclo[3,3,0]octane skeleton, and Reference Example 5 illustrates a novel process for the preparation of key intermediates containing that double ring system.

Thus, according to a feature of the present invention, key intermediates of the general formula shown in FIG. XII wherein $R^{14}$ represents an acyl group, more especially a lower alkanoyl (e.g. acetyl) group are prepared by the oxidation of compounds of the general formula shown in FIG. XIII wherein $R^{14}$ is as hereinbefore defined.

Preferably the oxidation is carried out by reaction with a thallium (III) salt, e.g. thallic nitrate, preferably in an organic acid medium, more especially glacial acetic acid, and preferably at an elevated temperature, e.g. 40°–120° C.

As an alternative, the oxidation is carried out by means of hydrogen peroxide in the presence of selenium dioxide. Conveniently the reaction may be carried out in tert-butanol as a solvent, and at an elevated temperature, e.g. 80° C.

The resulting compounds of the formula shown in FIG. XII can then be elaborated to form compounds of the formula shown in FIG. II by the application or adaptation of methods illustrated in the following Examples and Reference Examples.

Another important feature of the multistage process for the preparation of compounds of the formula shown in FIG. II is the formation of the side-chain in the 12-position, and Reference Example 22 illustrates the use of a novel reagent for the formation of a side-chain from a formyl group in the 12-position.

Thus, according to a further feature of the present invention, there are provided salts of dialkylphosphonates, of the general formula:

$$[M^1]^+[(R^{15}O)_2P(O)CHCO(CH_2)_4CH_3]^- \qquad XIV$$

(wherein $M^1$ represents an alkali metal atom such as a lithium or, more particularly, sodium atom, and $R^{15}$ represents an alkyl group of from 1 to 4 carbon atoms, preferably a methyl group) in their solid, isolated, form.

According to a feature of the present invention, compounds of formula XIV may be used in the application or adaptation of known methods for the conversion of formyl groups to 3-oxooct-1-enyl side-chains, for example, according to a feature of the invention, there is provided a process for the preparation of a compound of the general formula shown in FIG. XV (wherein $R^{16}$ represents a protected oxygen function such as an acyloxy, e.g. acetoxy, group or an ethylenedioxy group) by the reaction of a compound of the general formula shown in FIG. XVI (wherein $R^{16}$ is as hereinbefore defined) with a compound of the general formula XIV (wherein $M^1$ and $R^{15}$ are as hereinbefore defined), preferably in an inert organic solvent such as an ether (e.g. tetrahydrofuran) and preferably at or near room temperature, characterised in that the said compound or formula XIV is provided in its solid, isolated, form and not prepared in situ.

In the past, reagents such as those of formula XIV have been generated in situ by the action of a strong base such as an alkali metal hydride, e.g. sodium hydride, or an alkali metal alkyl, e.g. butyl lithium, on the parent dialkylphosphonates, usually in an inert organic solvent such as an ether, e.g. tetrahydrofuran.

Compounds of formula XIV may be prepared in their solid, isolated, form by the action of a strong base such as an alkali metal hydride, e.g. sodium hydride, or an alkali metal alkyl, e.g. butyl lithium, on phosphonates of the general formula:

$$(R^{15}O)_2P(O)CHCO(CH_2)_4CH_3 \qquad XVII$$

(wherein $R^{15}$ is as hereinbefore defined) in an inert organic solvent such as an ether, e.g. tetrahydrofuran, at or near room temperature and under an inert atmosphere, followed by filtration of the product under an inert atmosphere.

The use of compounds of formula XIV in their solid, isolated, form offers several important advantages over their preparation in situ, for example measurement of quantities is much easier so the use of an excess is not necessary, and so after the reaction the need to remove the excess is reduced or eliminated, there are fewer side-reactions, and the reaction generally is much cleaner.

It will be apparent to those skilled in the art that compounds of formula XIV may be used in the preparation of other important prostaglandins outside the scope of the formula shown in FIG. II, for example a prostaglandin compound having a 3-oxooct-1-enyl, 3-hydroxyoct-1-enyl, 3-oxooctyl or 3-hydroxyoctyl sidechain, more particularly PGE$_1$, PGE$_2$, PGF$_{2\alpha}$ and carbocyclin (i.e. the analogue of PGI$_2$ wherein the 6,9-epoxy group is replaced by a 6,9-methylene group), and this forms a further feature of the present invention.

Yet another important feature of the multistage process for the preparation of compounds of the formula shown in FIG. II is the formation of the side-chain in the 6-position, and Reference Examples 35, 39, 41, 47, 50 and 53 illustrates the novel use of a reagent in the formation of a side-chain in the 6-position.

Thus, according to a further feature of the present invention, there is provided a process for the preparation of a compound of the general formula shown in FIG. XVIII (wherein A$^1$, A$^2$, R$^2$, R$^3$, R$^4$, R$^5$, R$^6$ and Z$^1$ are as hereinbefore defined) from compounds of the general formula shown in FIG. XIX (wherein A$^2$, R$^4$, R$^5$ and Z$^1$ are as hereinbefore defined) by reaction with a compound of the general formula:

$$O=C(R^2)A^1CH(R^3)COOR^6 \qquad XX$$

(wherein A$^1$, R$^2$, R$^3$ and R$^6$ are as hereinbefore defined), preferably in an inert organic solvent such as an ether, e.g. tetrahydrofuran, preferably in dry conditions, preferably under an inert atmosphere, and preferably at a low temperature, e.g. $-78°$ C. to $-65°$ C., characterised in that the reaction is carried out in the presence of a compound of the general formula:

$$M^2[(R^{17})_3Si]_2N \qquad XXI$$

(wherein M$^2$ represents an alkali metal, preferably lithium, atom and R$^{17}$ represents an alkyl group of from 1 to 4 carbon atoms, preferably a methyl group).

The presence of a compound of formula XXI in the reaction mixture helps to minimise side reactions and to ensure that the side-chain becomes attached to the bicyclo[3,3,0]octane skeleton in the desired position.

The following Examples illustrate the preparation of the compounds of the present invention, and the Reference Examples illustrate the preparation of the intermediate compounds of the formula shown in FIG. VI. Reference Example 5 illustrates the preparation of the key intermediate compounds of the formula shown in FIG. XII. Reference Example 22 illustrates the use of a compound of formula XIV in its solid, isolated, form and Reference Example 55 illustrates its preparation. Reference Examples 35, 39, 41, 47, 50 and 53 illustrate the use of a reagent of formula XXI.

The compounds prepared in the Examples and Reference Examples contain various centres of chirality and the products are mixtures of all possible diastereoisomers unless otherwise specified, and each one is accompanied by an equal quantity of its enantiomer. However, the two hydrogen atoms attached to the bridgehead carbon atoms in the bicyclononane and bicyclooctane rings are always cis with respect to each other. According to the convention customarily employed, and with the structures laid out as in the formula drawings, the said hydrogen atoms attached to the bridgehead carbon atoms are said to be in the $\beta$-configuration, and the sidechain attached in the 12-position is cis with respect to the said hydrogen atoms when the said sidechain is said to be in the $\beta$-configuration. The designation ($\pm$) indicates that such compounds are accompanied by equal quantities of their enantiomers.

EXAMPLE 1

Compound A

6-[(E)-3-tert-Butyldimethylsilyloxy-3-cyclohexylprop-1-enyl]-3-[(E)-4-methoxycarbonylbutylidene]-bicyclo[3,3,0]octane-2-one (12 mg), prepared as described in Reference Example 15 and in the form of ($\pm$)-6$\beta$-[(E)-3$\beta$-tert-butyldimethylsilyloxy-3-cyclohexylprop-1-enyl]-3-[(E)-4-methoxycarbonylbutylidene]-bicyclo[3,3,0]octane-2-one, otherwise known as ($\pm$)-methyl(5E,13E)-(9S,15S)-6a-oxo-6,9-methano-15-tert-butyldimethylsilyloxy-15-cyclohexyl-16,17,18,19,20-pentanorprosta-5,13-dienoate, and a solution of water, glacial acetic acid and tetrahydrofuran (0.5 ml; 35:65:10 by volume) were stirred together at 40° C. for 4 hours. After cooling, the mixture was diluted with saturated aqueous sodium chloride solution and extracted with diethyl ether. The ethereal extracts were washed with aqueous sodium bicarbonate solution (1M) and then with saturated aqueous sodium chloride solution, and dried over anhydrous sodium sulphate. Concentration under reduced pressure gave 6-[(E)-3-cyclohexyl-3-hydroxyprop-1-enyl]-3-[(E)-4-methoxycarbonyl-butylidene]bicyclo[3,3,0]octan-2-one (12.7 mg), in the form of (3S)-6$\beta$-[(E)-3-cyclohexyl-3$\beta$-hydroxyprop-1-enyl]-3-[(E)-4-methoxycarbonylbutylidene]bicyclo[3,3,0]octan-2-one, otherwise known as ($\pm$)-methyl(-5E,13E)-(9S,15S)-6a-oxo-6,9-methano-15-cyclohexyl-15-hydroxy-16,17,18,19,20-pentanorprosta-5,13-dienoate.

EXAMPLE 2

Compound B

A mixture of 6-[(E)-3-cyclohexyl-3-hydroxyprop-1-enyl]-3-[(E)-4-methoxycarbonylbutylidene]bicyclo[3,3,0]octan-2-one (12.7 mg), prepared as described in Example 1 and in the form of ($\pm$)-6$\beta$-[(E)-3-cyclohexyl-3$\alpha$-hydroxyprop-1-enyl]-3-[(E)-4-methoxycarbonylbutylidene]bicyclo[3,3,0]octan-2-one, otherwise known as ($\pm$)methyl(5E,13E)-(9S,15S)-6a-oxo-6,9-methano-15-cyclohexyl-15-hydroxy-16,17,18,19,20-pentanorprosta-5,13-dienoate, lithium hydroxide (21.5 mg), methanol (2 ml), and water (0.7 ml) was left to stand at the ambient temperature for 1 hour. The mixture was then diluted with water (5 ml) and washed with dichloromethane. The aqueous layer was separated and acidified to pH 3 by treatment with aqueous hydrochloric acid (2N). The acidic solution was extracted with dichloromethane, and this extract was washed with saturated aqueous sodium chloride solution, dried over anhydrous sodium sulphate, and concentrated under reduced pressure, to give 3-[(E)-4-carboxybutylidene]-6-[(E)-3-cyclohexyl-3-hydroxyprop-1-enyl]bicyclo[3,3,0]octan-2-one (6.6 mg), in the form of ($\pm$)-3-[(E)-4-carboxybutylidene]-6$\beta$-[(E)-3-cyclohexyl-3$\alpha$-hydroxyprop-1-enyl]bicyclo[3,3,0]octan-2-one, otherwise known as ($\pm$)-(5E,13E)-(9S,15S)-6a-oxo-6,9-methano-15-cyclohexyl-15-hydroxy-16,17,18,19,20-pentanorprosta-5,13-dienoic acid.

EXAMPLE 3

Compound C

A solution of 3-[(E)-4-carboxybutylidene]-6-[(E)-3-cyclohexyl-3-hydroxyprop-1-enyl]bicyclo[3,3,0]octan- 2-one (6.6 mg), prepared as described in Example 2 and in the form of (±)-3-[(E)-4-carboxybutylidene]-6β-[(E)-3-cyclohexyl-3α-hydroxyprop-1-enyl]bicyclo[3,3,0]octan-2-one, otherwise known as (±)-(5E,13E)-(9S,15S)-6a-oxo-6,9-methano-15-cyclohexyl-15-hydroxy-16,17,18,19,20-pentanorprosta-5,13-dienoic acid in acetone (1 ml) and benzene (4 ml) was irradiated in a quartz vessel with ultra-violet rays of wavelength 254 nm, emitted by a low pressure mercury vapour lamp, for 20 hours. The solution was then concentrated under reduced pressure and subjected to preparative thin layer chromatography on silica gel, eluting four times with a mixture of ethyl acetate, hexane and formic acid (40:60:1 by volume).

The more polar component (0.8 mg) was unchanged starting material [NMR in deuterochloroform: multiplets at 6.5, 5.4, 3.8, 3.6, 1.0–3.0 p.p.m.].

The less polar component (1.2 mg) was (±)-3-{[mixture of (E) and (Z)]-4-carboxybutylidene}-6β-[(E)-3-cyclohexyl-3α-hydroxyprop-1-enyl]bicyclo[3,3,0]octan-2-one, otherwise known as (±)-[mixture of (5E) and (5Z)], (13E)-(9S,15S)-6a-oxo-6,9-methano-15-cyclohexyl-15-hydroxy-16,17,18,19,20-pentanorprosta-5,13-dienoic acid (1.2 mg). [NMR in deuterochloroform: multiplets at 6.5, 5.9, 5.8, 5.6, 5.4 and 1.0–3.0 p.p. m.]

The (Z)-isomer in the said less polar component slowly isomerised back to the (E)-isomer at the ambient temperature.

EXAMPLE 4

Compound D

6-[(E)-(mixture of 3α and 3β)-tert-Butyldimethylsilyloxyoct-1-enyl]-3-[(E)-4-methoxycarbonylbutylidene]bicyclo[3,3,0]octan-2-one (14.1 mg), prepared as described in Reference Example 27 or 28 and predominantly in the 6β-configuration, otherwise known as (±)-methyl(5E,13E)-(9S),[mixture of (15R) and (15S)]-6a-oxosilyloxyprosta-5,13-dienoate, and a solution of water, glacial acetic acid and tetrahydrofuran (0.5 ml; 7:13:2 by volume) were stirred together at 40° C. for 4 hours. After cooling, the mixture was diluted with saturated aqueous sodium chloride solution and extracted with diethyl ether. The ethereal extracts were washed with aqueous sodium bicarbonate solution (1M) and then with saturated aqueous sodium chloride solution, and then dried over anhydrous sodium sulphate. Concentration under reduced pressure gave 6-[(E)-(mixture of 3α and 3β)-hydroxyoct-1-enyl]-3-[(E)-4-methoxycarbonylbutylidene]bicyclo[3,3,0]octan-2-one (11.1 mg), predominantly in the 6β-configuration, otherwise known as (±)-methyl(5E,13E)-(9S),[mixture of (15R) and (15S)]-6a-oxo-6,9-methano-15-hydroxyprosta-5,13-dienoate. [NMR in deuterochloroform: multiplets at 6.5, 5.5, 4.1, 3.0–0.7 p.p.m., singlet at 3.7 p.p.m.; λ$_{max}$EtOH 244 nm, ε7,000].

EXAMPLE 5

Compound E

A stirred solution of 6-[(E)-(mixture of 3β and 3β)-hydroxyoct-1-enyl]-3-[(E)-4-methoxycarbonylbutylidene]bicyclo[3,3,0]octan-2-one (90 mg), prepared as described in Example 4 and predominantly in the 6β-configuration, otherwise known as (±)-methyl(-5E,13E)-(9S),[mixture of (15R) and (15S)]-6a-oxo-6,9-methano-15-hydroxyprosta-5,13-dienoate, in methanol (2 ml) at 5° C. was treated with aqueous lithium hydroxide solution (1.5 ml; 1.0N). The resulting solution was stirred for 3.3 hours at 10° C. and was then treated with glacial acetic acid (0.1 ml). The methanol was removed in vacuo and the residue was diluted with ethyl acetate (10 ml), washed with hydrochloric acid (2N), then with water, and then with saturated aqueous sodium chloride solution, dried over anhydrous sodium sulphate and concentrated in vacuo, to give 3-[(E)-4-carboxybutylidene]-6-[(E)-(mixture of 3α and 3β)-hydroxyoct-1-enyl]bicyclo[3,3,0]octan-2-one (70.0 mg), thought to be in the 6β-configuration, otherwise known as (±)-(5E,13E)-(9S),[mixture of (15R) and (15S)]-6a-oxo-6,9-methano-15-hydroxyprosta-5,13-dienoic acid [NMR in deuterochloroform: multiplets at 6.6, 5.5, 4.8–3.7, 3.0–1.1, 1.1–0.7 p.p.m.].

EXAMPLE 6

Compound F

A solution of 3-[(E)-4-carboxybutylidene]-6-[(E)-(mixture of 3α and 3β)-hydroxyoct-1-enyl]bicyclo[3,3,-0]octan-2-one (10 mg), prepared as described in Example 5 and predominantly in the 6β-configuration, otherwise known as (±)-(5E,13E)-(9S),[mixture of (15R) and (15S)]-6a-oxo-6,9-methano-15-hydroxyprosta-5,13-dienoic acid, in benzene (5 ml) and acetone (0.5 ml) was irradiated for 19 hours with ultra-violet rays of wavelength 254 nm, emitted by a low pressure mercury vapour lamp. The solution was then concentrated in vacuo and the residue was subjected to preparative thin layer chromatography on silica gel, using a mixture of ethyl acetate, hexane and glacial acetic acid (50:50:1 by volume) as eluant, to give 3-[(Z)-4-carboxybutylidene]-6-[(E)-(mixture of 3α and 3β)-hydroxyoct-1-enyl]bicyclo[3,3,0]octan-2-one (2.7 mg), predominantly in the 6β-configuration, otherwise known as (±)-(5Z,13E)-(9S),[mixture of (15R) and (15S)]-6a-oxo-6,9-methano-15-hydroxyprosta-5,13-dienoic acid [NMR (in deuterochloroform): multiplets at 6.0, 5.5, 4.5–3.8, 3.6–1.1, 1.1–0.7 p.p.m];

and recovered 3-[(E)-4-carboxybutylidene]-6-[(E)-(mixture of 3α and 3β)-hydroxyoct-1-enyl]bicyclo[3,3,-0]octan-2-one (3.6 mg).

EXAMPLE 7

Compound G

A solution of 6-[(E)-(mixture of 3α and 3β)-hydroxyoct-1-enyl]-3-[(E)-4-methoxycarbonylbutylidene]bicyclo[3,3,0]octan-2-one (20 mg), prepared as described in Example 4 and predominantly in the 6β-configuration, otherwise known as (±)-methyl(5E,13E)-(9S),[mixture of (15R) and (15S)]-6a-oxo-6,9-methano-15-hydroxyprosta-5,13-dienoate, in methanol (5 ml) was irradiated for 20 hours with ultra-violet rays of wavelength 254 nm, emitted by a low pressure mercury vapour lamp. The solution was carefully concentrated in vacuo and then subjected to preparative thin layer chromatography on silica gel, using a mixture of ethyl acetate and hexane (1:4 v/v) as eluant, to give 6-[(E)-(mixture of 3α and 3β)-hydroxyoct-1-enyl]-3-[(Z)-4-methoxycarbonylbutylidene]bicyclo[3,3,0]octan-2-one (5.0 mg), predominantly in the 6β-configuration, otherwise known as (±)-methyl(5Z,13E)-(9S),[mixture of (15R) and (15S)]-6a-oxo-6,9-methano-15-hydroxyprosta-5,13-dienoate [NMR in deuterochloroform: multiplets at 5.9, 5.5., 4.1, 3.0–1.1, 1.1–0.7 p.p.m., singlet at 3.7 p.p.m.]; and recovered 6-[(E)-(mixture of 3α and 3β)-hydroxyoct-1-enyl]-3-[(E)-4-methoxycarbonylbutylidene]-bicyclo[3,3,0]octan-2-one (3.6 mg) [NMR in deuterochloroform: multiplets at 6.5, 5.5, 4.1, 3.0–1.1, 1.1–0.7 p.p.m., singlet at 3.7 p.p.m.].

EXAMPLE 8

Compound H

A solution of 6-[(E)-(mixture of 3α and 3β)-tert-butyldimethylsilyloxy-3-cyclohexylprop-1-enyl]-3-[(E)-4-methoxycarbonylbutylidene]bicyclo[3,3,0]octan-2-one (43 mg), prepared as described in Reference Example 34 and predominantly in the 6β-configuration, otherwise known as (±)-methyl(5E,13E)-(9S),[mixture of (15R) and (15S)]-6a-oxo-6,9-methano-15-tert-butyldimethylsilyloxy-15-cyclohexyl-16,17,18,19,20-pentanorprosta-5,13-dienoate, in a mixture of tetrahydrofuran, glacial acetic acid and water (1 ml; 2:13:7 by volume) was stirred for 60 hours at 20° C. The solution was then concentrated in vacuo, to give 6-[(E)-3-cyclohexyl-(mixture of 3α and 3β)-hydroxyprop-1-enyl]-3-[(E)-4-methoxycarbonylbutylidene]bicyclo[3,3,0]octan-2-one (33 mg), predominantly in the 6β-configuration, otherwise known as (±)-methyl(5E,13E)-(9S),[mixture of (15R) and (15S)]-6a-oxo-6,9-methano-15-cyclohexyl-15-hydroxy-16,17,18,19,20-pentanorprosta-5,13-dienoate.

EXAMPLE 9

Compound I

A stirred solution of 6-[(E)-3-cyclohexyl-(mixture of 3α and 3β)-hydroxyprop-1-enyl]-3-[(E)-4-methoxycarbonylbutylidene]bicyclo[3,3,0]octan-2-one (20 mg), prepared as described in Example 8 and predominantly in the 6β-configuration, otherwise known as (±)-methyl(-5E,13E)-(9S),[mixture of (15R) and (15S)]-6a-oxo-6,9-methano-15-cyclohexyl-15-hydroxy-16,17,18,19,20-pentanorprosta-5,13-dienoate, in methanol (3.2 ml) was treated with lithium hydroxide (33.8 mg) and water (1.1 ml) at 20° C. and stirred for 2 hours. The mixture was then concentrated in vacuo. The resulting residue was diluted with water (5 ml) and then acidified to pH 3 by treatment with dilute hydrochloric acid (2N). The aqueous layer was then extracted with ethyl acetate (5×5 ml). The combined organic extracts were dried over anhydrous sodium sulphate and concentrated in vacuo. The resulting residue was subjected to chromatography on a silica gel column, using a mixture of ethyl acetate, hexane and formic acid (50:50:1 by volume) as eluant, to give 3-[(E)-4-carboxybutylidene]-6-[(E)-3-cyclohexyl-(mixture of 3α and 3β)-hydroxyprop-1-enyl]bicyclo[3,3,0]octan-2-one (10 mg), predominantly in the 6β-configuration, otherwise known as (±)-(5E,13E)-(9S),[mixture of (15R) and (15S)]-6a-oxo-6,9-methano-15-cyclohexyl-15-hydroxy-16,17,18,19,20-pentanorprosta-5,13-dienoic acid [NMR in deuterochloroform: multiplets at 6.5, 5.5, 4.2–3.5, 3.0–0.7 p.p.m.].

EXAMPLE 10

Compound J

A stirred solution of 6-[(E)-3-cyclohexyl-(mixture of 3α and 3β)-hydroxyprop-1-enyl]-3-[(E)-4-methoxycarbonylbutylidene]bicyclo[3,3,0]octan-2-one (6.7 mg), prepared as described in Example 8 and predominantly in the 6β-configuration, otherwise known as (±)-methyl(5E,13E)-(9S),[mixture of (15R) and (15S)]-6a-oxo-6,9-methano-15-cyclohexyl-15-hydroxy-16,17,18,19,20-pentanorprosta-5,13-dienoate, in tetrahydrofuran (0.5 ml) at −78° C. was treated dropwise with a solution of lithium tri-sec-butylborohydride in tetrahydrofuran (0.0196 ml; 1.0M). The stirred solution was allowed to warm to 0° during 2 hours and then it was stirred for a further period of 2 hours. Glacial acetic acid (0.15 ml) and water (0.2 ml) were then added to the mixture, which was then concentrated in vacuo. The resulting residue was dissolved in ethyl acetate (10 ml), washed with aqueous sodium bicarbonate solution (2M) and then with saturated aqueous sodium chloride solution, dried over anhydrous sodium sulphate and concentrated in vacuo. The resulting oil was treated with a solution of sodium hydroxide in 50% v/v aqueous methanol (0.1 ml; 2.5N) and stirred for 150 minutes at 20° C. The mixture was then carefully concentrated in vacuo, and diluted with water (6 ml) and diethyl ether (3 ml). The aqueous phase was separated, acidified to pH 3 by treatment with hydrochloric acid (2N), and extracted with ethyl acetate (4×10 ml). The combined organic extracts were dried over sodium sulphate and concentrated in vacuo. The resulting residue was subjected to chromatography on a silica gel column, using a mixture of ethyl acetate, hexane and glacial acetic acid (50:50:1 by volume) as eluant, to give 3-[(E)-4-carboxybutylidene]-6-[(E)-3-cyclohexyl-(mixture of 3α and 3β)-hydroxyprop-1-enyl]-2-hydroxybicyclo[3,3,0]octane (3.6 mg), predominantly in the 6β,6α-configuration, otherwise known as (±)-(5E,13E)-(6aS,9S),[mixture of (15R) and (15S)]-6a,15-dihydroxy-6,9-methano-15-cyclohexyl-16,17,18,19,20-pentanorprosta-5,13-dienoic acid [NMR in deuterochloroform: multiplets at 5.5, 3.5, 2.7–0.7 p.p.m.].

EXAMPLE 11

Compound K (E)-6-(3-tert-Butyldimethylsilyloxy-3-cyclohexylprop-1-enyl)-3-(4-ethoxycarbonylcyclohexylidene)-bicyclo[3,3,0]octan-2-one (15 mg), prepared as described in Reference Example 36 and in the form of (±)-(E)-6β-(3α-tert-butyldimethylsilyloxy-3-cyclohexylprop-1-enyl)-3-(4-ethoxycarbonylcyclohexylidene)-bicyclo[3,3,0]-octan-2-one, otherwise known as (±)-ethyl(13E)-(9S,15S)-6a-oxo-2,5-ethano-6,9-methano-15-tert-butyldimethylsilyloxy-15-cyclohexyl-16,17,18,19,20-pentanorprosta-5,13-dienoate and a solution of water, glacial acetic acid and tetrahydrofuran (0.59 ml; 7:13:2 by volume) were stirred together at 45° C. for 5 hours. After cooling, the mixture was diluted with saturated aqueous sodium chloride solution and extracted with ethyl acetate. The extract was washed with aqueous sodium carbonate solution (2M) and then with saturated aqueous sodium chloride solution, dried over anhydrous sodium sulphate, and concentrated under reduced pressure. The residue was subjected to medium pressure, short column chromatography on silica gel, using a mixture of ethyl acetate and hexane (2:1 v/v) as eluant, to give (E)-6-(3-cyclohexyl-3-hydroxyprop-1-enyl)-3-(4-ethoxycarbonylcyclohexylidene)bicyclo[3,3,0]octan-2-one (8.6 mg), in the form of (±)-(E)-6β-(3-cyclohexyl-3α-hydroxyprop-1-enyl)-3-(4-ethoxycarbonylcyclohexylidene)bicyclo[3,3,0]octan-2-one, otherwise known as (±)-ethyl(13E)-(9S,15S)-6a-oxo-2,5-ethano-6,9-methano-15-hydroxy-15-cyclohexyl-16,17,18,19,20-pentanorprosta-5,13-dienoate [NMR (in deuterochloroform): multiplets at 5.4–5.6, 3.6–4.3 and 0.8–3.0 p.p.m.].

EXAMPLE 12

Compound L

By proceeding in a manner similar to that described in Example 1, but replacing the starting material by the appropriate quantity of 6-[(E)-3-tert-butyldimethylsilyloxy-3-cyclohexylprop-1-enyl]-3-[(E)-4-methoxycarbonylbutylidene]bicyclo[3,3,0]octan-2-one, prepared as described in Reference Example 38 and in the form of (±)-6β-[(E)-3β-tert-butyldimethylsilyloxy-3-cyclohexylprop-1-enyl]-3-[(E)-4-methoxycarbonylbutylidene]bicyclo[3,3,0]octan-2-one, otherwise known as (±)-methyl(5E,13E)-(9S,15R)-6a-oxo-6,9-methano-15-tert-butyldimethylsilyloxy-15-cyclohexyl-16,17,18,19,20-pentanorprosta-5,13-dienoate, there was prepared 6-[(E)-3-cyclohexyl-3-hydroxyprop-1-enyl]-3-[(E)-4-methoxycarbonylbutylidene]bicyclo[3,3,0]octan-2-one, in the form of (±)-6 β-[(E)-3-cyclohexyl-3β-hydroxyprop-1-enyl]-3-[(E)-4-methoxycarbonylbutylidene]-bicyclo[3,3,0]octan-2-one, otherwise known as (±)-methyl(5E,13E)-(9S,15R)-6a-oxo-6,9-methano-15-cyclohexyl-15-hydroxy-16,17,18,19,20-pentanorprosta-5,13-dienoate.

EXAMPLE 13

Compound M

By proceeding in a manner similar to that described in Example 2, but replacing the starting material by the appropriate quantity of 6-[(E-3E-cyclohexyl-3-hydroxyprop-1-enyl]-3-[(E)-4-methoxycarbonylbutylidene]-bicyclo[3,3,0]octan-2-one, prepared as described in Example 12 and in the form of (±)-6β-[(E)-3-cyclohexyl-3β-hydroxyprop-1-enyl]-3-[(E)-4-methoxycarbonylbutylidene]bicyclo[3,3,0]octan-2-one, otherwise known as (±)-methyl(5E,13E)-(9S,15R)-6a-oxo-6,9-methano-15-cyclohexyl-15-hydroxy-16,17,18,19,20-pentanorprosta-5,13-dienoate, there was prepared 3-[(E)-4-carboxybutylidene]-6-[(E)-3-cyclohexyl-3-hydroxyprop-1-enyl]bicyclo[3,3,0]octan-2-one, in the form of (±)-3-[(E)-4-carboxybutylidene]-6β-[(E)-3-cyclohexyl-3β-hydroxyprop-1-enyl]bicyclo[3,3,0]octan-2-one, otherwise known as (±)-(5E,13E)-(9S,15R)-6a-oxo-6,9-methano-15-cyclohexyl-15-hydroxy-16,17,18,19,20-pentanorprosta-5,13-dienoic acid [NMR (in deuterochloroform):-multiplets at 6.3–6.6, 5.3–5.6, 4.3–4.8, 4.0–4.3, 1.0–3.0p.p.m.].

EXAMPLE 14

Compound N

By proceeding in a manner to that described in Example 11, but replacing the starting material by the appropriate quantity of 6-[(E)-3-tert-butyldimethylsilyloxy-3-cyclohexylprop-1-enyl]-3-{[mixture of (E) and (Z)]-5-ethoxycarbonylpentylid-2-ene}bicyclo[3,3,0]octan-2-one, prepared as described in Reference Example 40 and in the form of (±)-6β-[(E)-3β-tert-butyldimethylsilyloxy-3-cyclohexylprop-1-enyl]-3-{[mixture of (E) and (Z)]-5-ethoxycarbonylpentylid-2-ene}bicyclo[3,3,-0]octan-2-one, otherwise known as (±)-ethyl [mixture of (5E) and (5Z)], (13E)-(9S,15R)-6a-oxo-6,9-methano-5-methyl-15-tert-butyldimethylsilyloxy-15-cyclohexyl-16,17,18,19,20-pentanorprosta-5,13-dienoate, there was prepared 6-[(E)-3-cyclohexyl-3-hydroxyprop-1-enyl]-3-{[mixture of (E) and (Z)]-5-ethoxycarbonylpentylid-2-ene}bicyclo[3,3,0]octan-2-one, in the form of (±)-6β-[(E)-3-cyclohexyl-3β-hydroxyprop-1-enyl]-3-{[mixture of (E) and (Z)]-5-ethoxycarbonylpentylid-2-ene}bicyclo[3,3,0]octan-2-one, otherwise known as (±)-ethyl [mixture of (5E) and (5Z)], (13E)-(9S,15R)-6a-oxo-6,9-methano-5-methyl-15-cyclohexyl-15-hydroxy-16,17,18,19,20-pentanorprosta-5,13-dienoate [NMR (in deuterochloroform): 5.3–5.6, 3.9–4.3, 3.6–3.9, 1.0–2.2 p.p.m.].

EXAMPLE 15

Compound O

By proceeding in a manner similar to that described in Example 11, but replacing the starting material with the appropriate quantity of (E)-6-(3-tert-butyldimethylsilyloxy-3-cyclohexylprop-1-enyl)-3-(4-ethoxycarbonylcyclohexylidene)bicyclo[3,3,0]octan-2-one, prepared as described in Reference Example 42 and in the form of (±)-(E)-6β-(3β-tert-butyldimethylsilyloxy-3-cyclohexylprop-1-enyl)-3-(4-ethoxycarbonylcyclohexylidene)bicyclo[3,3,0]octan-2-one, otherwise known as (±)-ethyl (13E)-(9S,15R)-6a-oxo-2,5-ethano-6,9-methano-15-tert-butyldimethylsilyloxy-15-cyclohexyl-16,17,18,19,20-pentanorprosta-5,13-dienoate, there was prepared (E)-6-(3-cyclohexyl-3-hydroxyprop-1-enyl)-3-(4-ethoxycarbonylcyclohexylidene)bicyclo[3,3,0]octan-2-one, in the form of (±)-(E)-6β-(3-cyclohexyl-3β-hydroxyprop-1-enyl)-3-(4-ethoxycarbonylcyclohexylidene)bicyclo[3,3,0]octan-2-one, otherwise known as (±)-ethyl (13E)-(9S,15R)-6a-oxo-2,5-ethano-6,9-methano-15-hydroxy-15-cyclohexyl-16,17,18,19,20-pentanorprosta-5,13-dienoate [NMR (in deuterochloroform): multiplets at 5.3–5.6, 3.6–4.5, 0.7–3.2 p.p.m.].

EXAMPLE 16

Compound P

6-[(E)-3-tert-Butyldimethylsilyloxy-4-phenoxybut-1-enyl)]-3-[(E)-4-methoxycarbonylbutylidene]-bicyclo[3,3,0]octan-2-one (21 mg), prepared as described in Reference Example 48 and in the form of (±)-6β-[(E)-3β-tert-butyldimethylsilyloxy-4-phenoxybut-1-enyl]-3-[(E)-4-methoxycarbonylbutylidene]bicyclo[3,3,0]octan-2-one, otherwise known as (±)-methyl (5E,13E)-(9S,15S)-6a-oxo-6,9-methano-15-tert-butyldimethylsilyloxy-16-phenoxy-17,18,19,20-tetranorprosta-5,13-dienoate, and a solution of water, glacial acetic acid and tetrahydrofuran (0.86 ml; 7:13:2 by volume) were stirred together at 40° C. for 4 hours. After cooling, the mixture was diluted with saturated aqueous sodium chloride solution and extracted with diethyl ether. The ethereal extract was washed with aqueous sodium bicarbonate solution (1M) and then with saturated aqueous sodium chloride solution, dried over anhydrous sodium sulphate and concentrated under reduced pressure. The residue was subjected to medium pressure chromatography on silica gel, eluting with a mixture of ethyl acetate and hexane (1:1 v/v), to give 6-[(E)-3-hydroxy-4-phenoxybut-1-enyl]-3-[(E)-4-methoxycarbonylbutylidene]bicyclo[3,3,0]octan-2-one (15.9 mg), in the form of (±)-6β-[(E)-3β-hydroxy-4-phenoxybut-1-enyl]-3-[(E)-4-methoxycarbonylbutylidene]bicyclo[3,3,0]octan-2-one, otherwise known as (±)-methyl (5E,13E)-(9S,15S)-6a-oxo-6,9-methano-15-hydroxy-16-phenoxy-17,18,19,20-tetranorprosta-5,13-dienoate [NMR (in deuterochloroform): multiplets at 6.6–7.2, 6.3–6.6, 5.3–5.6, 4.3–4.5, 3.7–3.9, 1.3–2.8 p.p.m., singlet at 3.6 p.p.m.].

EXAMPLE 17

Compound Q

6-[(E)-3-tert-Butyldimethylsilyloxy-4-phenoxybut-1-enyl]-3-[(E)-4-methoxycarbonylbutylidene]bicyclo[3,3,0]octan-2-one (13 mg), prepared as described in Reference Example 51 and in the form of (±)-6β-[(E)-3α-tert-butyldimethylsilyloxy-4-phenoxybut-1-enyl]-3-[(E)-4-methoxycarbonylbutylidene]bicyclo[3,3,0]octan-2-one, otherwise known as (±)-methyl (5E,13E)-(9S,15R)-6a-oxo-6,9-methano-15-tert-butyldimethylsilyloxy-16-phenoxy-17,18,19,20-tetranorprosta-5,13-dienoate, and a solution of water, glacial acetic acid and tetrahydrofuran (0.53 ml; 7:13:2 by volume) were stirred together at 40° C. for 4 hours. After cooling, the mixture was diluted with saturated aqueous sodium chloride solution and extracted with diethyl ether. The extract was washed with aqueous sodium bicarbonate solution (1M) and then with saturated aqueous sodium chloride solution, dried over anhydrous sodium sulphate, and concentrated under reduced pressure. The residue was subjected to medium pressure liquid chromatography on silica gel, eluting with a mixture of ethyl acetate and hexane (9:13 v/v), to give 6-[(E)-3-hydroxy-4-phenoxybut-1-enyl]-3-[(E)-4-methoxycarbonylbutylidene]bicyclo[3,3,0]octan-2-one (9.9 mg), in the form of (±)-6β-[(E)-3α-hydroxy-4-phenoxybut-1-enyl]-3-[(E)-4-methoxycarbonylbutylidene]bicyclo[3,3,0]octan-2-one, otherwise known as (±)-methyl (5E,13E)-(9S,15R)-6a-oxo-6,9-methano-15-hydroxy-16-phenoxy-17,18,19,20-tetranorprosta-5,13-dienoate [NMR (in deuterochloroform): multiplets at 6.8–7.3, 6.4–6.6, 5.6–5.8, 4.3–4.6, 3.8–4.0, 1.3–2.8 p.p.m., singlet at 3.6 p.p.m.].

EXAMPLE 18

Compound R

6-[(E)-3-tert-Butyldimethylsilyloxy-4-phenoxybut-1-enyl]-3-[(E)-4-methoxycarbonylbutylidene]bicyclo[3,3,0]octan-2-one (4.1 mg), prepared as described in Reference Example 54, and in the form of (±)-6β-[(E)-(mixture of 3α and 3β)-tert-butyldimethylsilyloxy-4-phenoxybut-1-enyl]-3-[(E)-4-methoxycarbonylbutylidene]bicyclo[3,3,0]octan-2-one, otherwise known as (±)-methyl (5E,13E)-(9S), [mixture of (15R) and (15S)]-6a-oxo-6,9-methano-15-tert-butyldimethylsilyloxy-16-phenoxy-17,18,19,20-tetranorprosta-5,13-dienoate, and a solution of water, glacial acetic acid and tetrahydrofuran (1.0 ml; 7:13:2 by volume) were stirred together at 40° C. for 4 hours. After cooling, the mixture was diluted with saturated aqueous sodium chloride solution and extracted with diethyl ether. The extract was washed with aqueous sodium bicarbonate solution (1M) and then with saturated aqueous sodium chloride solution, dried over anhydrous sodium sulphate and concentrated under reduced pressure. The residue (3.0 mg) was subjected to preparative thin layer chromatography on silica gel, eluting with a mixture of ethyl acetate and hexane (3:2 v/v), to give 6-[(E)-3-hydroxy-4-phenoxybut-1-enyl]-3-[(E)-4-methoxycarbonylbutylidene]bicyclo[3,3,0]octan-2-one (0.9 mg), in the form of (±)-6β-[(E)-(mixture of 3α and 3β)-hydroxy-4-phenoxybut-1-enyl]-3-[(E)-4-methoxycarbonylbutylidene]bicyclo[3,3,0]octan-2-one, otherwise known as (±)-methyl (5E,13E)-(9S), [mixture of (15R) and (15S)]-6a-oxo-6,9-methano-15-hydroxy-16-phenoxy-17,18,19,20-tetranorprosta-5,13-dienoate.

REFERENCE EXAMPLE 1

2-Methoxybutadiene (69.9 g), 2-cyclopentenone (68.22 g) and hydroquinone (0.2 g) were heated together at 190° C. for 2 hours. The product was then distilled in vacuo, to give 3-methoxybicyclo[4,3,0]non-3-en-7-one (30 g), b.p. 74°–92° C./1.5 mmHg.

REFERENCE EXAMPLE 2

Diisobutylaluminium hydride (28.5 ml) was added dropwise to a stirred solution of 3-methoxybicyclo[4,3,0]non-3-en-7-one (20 g; prepared as described in Reference Example 1) in diethyl ether (600 ml), with cooling to −10° C. The resulting solution was stirred at 0° C. for 3 hours and then it was treated with methanol (20 ml). A gelatinous precipitate was formed, and the mixture was then treated with anhydrous sodium sulphate (200 g) and filtered with the aid of diatomaceous earth. The filtrate was concentrated at reduced pressure, to give 7-hydroxy-3-methoxybicyclo[4,3,0]non-3-ene (16 g).

REFERENCE EXAMPLE 3

Acetic anhydride (62.3 g) was added to a solution of 7-hydroxy-3-methoxybicyclo[4,3,0]non-3-ene (51.4 g; prepared as described in Reference Example 2) in pyridine (166 ml), and the mixture was left to stand at the ambient temperature for 60 hours. Concentration under reduced pressure gave 7-acetoxy-3-methoxybicyclo[4,3,0]non-3-ene (58.9 g).

REFERENCE EXAMPLE 4

Concentrated hydrochloric acid (3.5 ml) was added to a solution of 7-acetoxy-3-methoxybicyclo[4,3,0]non-3-ene (58.9 g; prepared as described in Reference Example 3) in methanol (500 ml), and the mixture was stirred at the ambient temperature for 5 minutes. It was then concentrated under reduced pressure, to give 7-acetoxybicyclo[4,3,0]nonan-3-one (54.7 g).

REFERENCE EXAMPLE 5

Thallic nitrate trihydrate (133 g) was added to a stirred solution of 7-acetoxybicyclo[4,3,0]nonan-3-one (57 g; prepared as described in Reference Example 4) in glacial acetic acid (290 ml). After 30 minutes the resulting solid was filtered off and the filtrate was heated at reflux for 30 minutes. The acetic acid was distilled off under reduced pressure and the residue was neutralised by treatment with aqueous sodium hydroxide solution to pH 5 and then with aqueous sodium bicarbonate solution to neutral. The resulting solution was washed with diethyl ether, and then it was acidified by treatment with concentrated hydrochloric acid and extracted with chloroform. The combined chloroform extracts were washed with saturated aqueous sodium chloride solution, then dried over magnesium sulphate, and concentrated under reduced pressure. The residue was purified by medium pressure, short column chromatography on silica gel, eluting with a mixture of ethyl acetate, hexane, and acetic acid (45:55:1 by volume), to give 6-acetoxy-2-carboxybicyclo[3,3,0]octane (7.55 g), predominantly in the 2β-configuration.

REFERENCE EXAMPLE 6

A mixture of 6-acetoxy-2-carboxybicyclo[3,3,0]octane (2.23 g; prepared as described in Reference Example 5 and predominantly in the 2β-configuration), methanol (25 ml), and concentrated hydrochloric acid (0.15 ml), was heated at reflux for 16 hours. The mixture was then concentrated under reduced pressure to a third of its previous volume, and it was then added to an excess of water. The mixture was extracted with dichloromethane. The combined dichloromethane extracts were washed with saturated aqueous sodium bicarbonate solution, and then with saturated aqueous sodium chloride solution, and then it was dried over anhydrous sodium sulphate. Concentration under reduced pressure gave crude 6-hydroxy-2-methoxycarbonylbicyclo[3,3,-0]octane (1.98 g), predominantly in the 2β-configuration, and pure enough for use in the next stage.

REFERENCE EXAMPLE 7

A solution of crude 6-hydroxy-2-methoxycarbonyl-bicyclo[3,3,0]octane (1.98 g; prepared as described in Reference Example 6 and predominantly in the 2β-configuration) in dichloromethane (10 ml) was added to a stirred suspension of pyridinium chlorochromate (3.5 g) in dichloromethane (35 ml), and the mixture was stirred for 2 hours. The mixture was then diluted with diethyl ether (200 ml), and the supernatant liquid was decanted onto a short column of silica gel. The residue was triturated with diethyl ether several times until it became granular in aspect and then all the ethereal washings were added to the column. The column was eluted with diethyl ether and the eluate was evaporated, to give crude 2-methoxycarbonylbicyclo[3,3,0]octan-6-one (1.71 g) [infra-red (I.R.) 1740 cm$^{-1}$], predominantly in the 2β-configuration, and pure enough for use in the next stage.

REFERENCE EXAMPLE 8

A mixture of crude 2-methoxycarbonylbicyclo[3,3,-0]octan-6-one (1.35; prepared as described in Reference Example 7 and predominantly in the 2β-configuration), ethylene glycol (1.84 g), benzene (100 ml), and a trace of p-toluenesulphonic acid was heated at reflux for 16 hours, collecting the water that formed in a Dean and Stark apparatus. After cooling, the mixture was diluted with diethyl ether, and washed successively with aqueous sodium carbonate solution (1M) and then with saturated aqueous sodium chloride solution, and then it was dried over anhydrous sodium sulphate. Concentration under reduced pressure gave crude spiro{6-methoxycarbonylbicyclo[3,3,0]octane-2,2'-dioxolane} (1.56 g) [I.R. 940, 1730 cm$^{-1}$], predominantly in the 6β-configuration, and pure enough to use in the next stage.

REFERENCE EXAMPLE 9

A solution of spiro{6-methoxycarbonylbicyclo[3,3,-0]octane-2,2'-dioxolane} (0.9 g; prepared as described in Reference Example 8 and predominantly in the 6β-configuration) in anhydrous tetrahydrofuran (4 ml) was added slowly to a stirred solution of lithium tri-sec-butylborohydride in tetrahydrofuran (12.2 ml; 1M) at −78° C. in an atmosphere of argon. The solution was stirred at −78° C. for 1 hour and was then stirred at the ambient temperature for 2 hours. The mixture was then treated with aqueous sodium hydroxide solution (9.3 ml; 3M), keeping the temperature at 0° C. The mixture was then treated slowly with aqueous hydrogen peroxide solution (6.3 ml; 30% w/v), keeping the temperature at 0° C., and then the mixture was stirred at 0° C. for a further period of 30 minutes. The mixture was then diluted with water and treated with sufficient sodium chloride to form a saturated solution and then it was extracted with diethyl ether. The combined extracts were washed with saturated aqueous sodium chloride solution and dried over anhydrous sodium sulphate and then concentrated under reduced pressure. The residue (0.77 g) was subjected to medium pressure, short column chromatography on silica gel using a mixture of ethyl acetate and methanol (40:1 v/v) as eluant, to give spiro{6-hydroxymethylbicyclo[3,3,0]octane-2,2'-dioxolane} (0.45 g), I.R. 3400 cm$^{-1}$, predominantly in the 6β-configuration.

REFERENCE EXAMPLE 10

A solution of spiro{6-hydroxymethylbicyclo[3,3,-0]octane-2,2'-dioxolane} (0.45 g; prepared as described in Reference Example 9 and predominantly in the 6β-configuration) in dichloromethane (2.1 ml) was added to a stirred suspension of pyridinium chlorochromate (0.74 g) in dichloromethane (7.5 ml). The mixture was stirred at the ambient temperature for 3 hours, and was then treated with an excess of diethyl ether. A gum separated, and the supernatant liquid was added carefully to the top of a short silica gel chromatography column. The gum was triturated several times with diethyl ether until it became granular in aspect. The ethereal solutions and the granules were also added to the top of the column. The column was then eluted with diethyl ether, and the combined eluant was concentrated in vacuo, to give spiro{6-formylbicyclo[3,3,0]octane-2,2'-dioxolane} (0.37 g), predominantly in the 6β-configuration.

REFERENCE EXAMPLE 11

Dimethyl (2-cyclohexyl-2-oxoethyl)phosphonate (0.53 g) was added to a stirred suspension of sodium hydride dispersion (106 mg; 50% w/w in mineral oil) in dry tetrahydrofuran (16 ml) in an argon atmosphere and the mixture was stirred for 16 hours at room temperature. Spiro{6-formylbicyclo[3,3,0]octane-2,2'-dioxolane} (0.37 g; prepared as described in Reference Example 10 and predominantly in the 6β-configuration) was then added, and the mixture was stirred for a further period of 2 hours. The mixture was then concentrated under reduced pressure, and the residue was dissolved in diethyl ether. The ethereal solution was washed with water, dried over sodium sulphate and concentrated under reduced pressure. The residue was subjected to medium pressure, short column chromatography on silica gel, using a mixture of ethyl acetate and hexane (1:3 v/v) as eluant, to give (E)-spiro{6-(3-cyclohexyl-3-oxoprop-1-enyl)bicyclo[3,3,0]octane-2,2'-dioxolane} (0.28 g), predominantly in the 6β-configuration.

REFERENCE EXAMPLE 12

A solution of (E)-spiro{6-(3-cyclohexyl-3-oxoprop-1-enyl)bicyclo[3,3,0]octane-2,2'-dioxolane} (0.28 g; prepared as described in Reference Example 11 and predominantly in the 6β-configuration) in dry tetrahydrofuran (1.0 ml) was added to a stirred solution of lithium tri-sec-butylborohydride in tetrahydrofuran (1.88 ml; 1M) at −78° C. under an atmosphere of argon. The mixture was stirred at −78° C. for 1 hour and then at ambient temperature for 2 hours. It was then treated with aqueous sodium hydroxide solution (1.34 ml; 3M) at 0° C., followed by aqueous hydrogen peroxide solution (0.88 ml; 30% w/v), and the mixture was stirred for a further period of 30 minutes at 0° C. The mixture was treated with water and sufficient sodium chloride to form a saturated solution, and then it was extracted with diethyl ether. The extract was washed with saturated aqueous sodium chloride solution and then dried over anhydrous sodium sulphate, and concentrated under reduced pressure, to give (E)-spiro{6-(3-cyclohexyl-3-hydroxyprop-1-enyl)bicyclo[3,3,0]octane-2,2'-dioxolane} (0.28 g), predominantly in the 6β-configuration and pure enough for use in the next stage.

REFERENCE EXAMPLE 13

A mixture of (E)-spiro{6-(3-cyclohexyl-3-hydroxyprop-1-enyl)bicyclo[3,3,0]octane-2,2'-dioxolane} (0.28 g; prepared as described in Reference Example 12 and predominantly in the 6β-configuration) and 60% w/v aqueous acetic acid was left to stand at ambient temperature for 16 hours. An excess of water was then added and the mixture was extracted with diethyl ether. The combined ethereal extracts were washed with aqueous sodium carbonate solution (1M) and then with saturated aqueous sodium chloride solution, dried over anhydrous sodium sulphate and concentrated under reduced pressure, to give (E)-2-(3-cyclohexyl-3-hydroxyprop-1-enyl)bicyclo[3,3,0]octan-6-one (0.23 g), predominantly in the 2β-configuration. This material was purified and separated into 2 epimeric pairs of enantiomers by short column chromatography on silica gel, eluting with a mixture of ethyl acetate and hexane (1:3 v/v). The less polar component (89 mg) was (±)-(E)-2β-(3-cyclohexyl-3β-hydroxyprop-1-enyl)bicyclo[3,3,0]octan-6-one and the more polar component (41 mg) was (±)-(E)-2β-(3-cyclohexyl-3α-hydroxyprop-1-enyl)bicyclo[3,3,0]octan-6-one.

REFERENCE EXAMPLE 14

A mixture of (E)-2-(3-cyclohexyl-3-hydroxyprop-1-enyl)bicyclo[3,3,0]octan-6-one (41 mg), prepared as described in Reference Example 13, and in the form of (±)-(E)-2β-(3-cyclohexyl-3α-hydroxyprop-1-enyl)-bicyclo[3,3,0]octan-6-one, tert-butyldimethylchlorosilane (35 mg), and imidazole (29.5 mg) in dimethylformamide (0.25 ml) was stirred at ambient temperature for 3 hours. Water (2.5 ml) was added and the mixture was extracted with diethyl ether. The combined ethereal extracts were washed with saturated aqueous sodium chloride solution, then dried over anhydrous sodium sulphate, and concentrated under reduced pressure to give (E)-2-(3-tert-butyldimethylsilyloxy-3-cyclohexylprop-1-enyl)bicyclo[3,3,0]octan-6-one (57 mg), in the form of (±)-(E)-2β-(3α-tert-butyldimethylsilyloxy-3-cyclohexylprop-1-enyl)bicyclo[3,3,0]octan-6-one.

REFERENCE EXAMPLE 15

(E)-2-(3-tert-Butyldimethylsilyloxy-3-cyclohexylprop-1-enyl)bicyclo[3,3,0]octan-6-one (57 mg), prepared as described in Reference Example 14 and in the form of (±)-(E)-2β-(3α-tert-butyldimethylsilyloxy-3-cyclohexylprop-1-enyl)bicyclo[3,3,0]octan-6-one, was dissolved in dry diethyl ether (0.6 ml). The solution was cooled to −70° C. under an atmosphere of argon and treated with a solution of lithium diisopropylamide in diethyl ether (0.132 ml; 1.3M) with stirring, and the mixture was stirred at −70° C. for 10 minutes. 4-Methoxycarbonylbutanal (29.6 mg) was then added to the mixture, which was stirred for a further period of 10 minutes at −70° C. The mixture was then treated with a solution of glacial acetic acid (0.05 ml) in diethyl ether (1 ml) and the mixture was allowed to warm to ambient temperature. Water and diethyl ether were added and the layers were separated. The aqueous layer was extracted with ethyl acetate. The combined diethyl ether and ethyl acetate solutions were washed with saturated aqueous sodium bicarbonate solution and then with saturated aqueous sodium chloride solution, dried over anhydrous sodium sulphate, and concentrated under reduced pressure. The resulting residue was dissolved in dry benzene (0.6 ml). The solution was treated with methanesulphonyl chloride (0.015 ml) with stirring at the ambient temperature, and then with triethylamine (0.0255 ml), and was stirred for a further period of 2 hours. The mixture was then treated with 1,8-diazabicyclo[5,4,0]undec-7-ene (137 mg) and stirred for 16 hours at ambient temperature. The crude mixture was then subjected to medium pressure, short column chromatography on silica gel, eluting with a mixture of ethyl acetate and hexane (1:9 by volume), to give (E)-6-(3-tert-butyldimethylsilyloxy-3-cyclohexylprop-1-enyl)-3-[(E)-4-methoxycarbonylbutylidene]bicyclo[3,3,0]octan-2-one (12 mg), in the form of (±)-6β-[(E)-3α-tert-butyldimethylsilyloxy-3-cyclohexylprop-1-enyl]-3-[(E)-4-methoxycarbonylbutylidene]bicyclo[3,3,0]octan-2-one, otherwise known as (±)-methyl (5E,13E)-(9S,15S)-6a-oxo-6,9-methano-15-tert-butyldimethylsilyloxy-15-cyclohexyl-16,17,18,19,20-pentanorprosta-5,13-dienoate.

REFERENCE EXAMPLE 16

The sodium salt of dimethyl (2-oxoheptyl)phosphonate (325 mg) was added to a stirred solution of spiro{6-formylbicyclo[3,3,0]octane-2,2'-dioxolane} (125 mg; prepared as described in Reference Example 10 and predominantly in the 6β-configuration) and the suspension was stirred at the ambient temperature under an argon atmosphere for 16 hours. Glacial acetic acid (6 drops) was then added, and the mixture was concentrated under reduced pressure. The residue was dissolved in water, and extracted with diethyl ether. The extract was dried over anhydrous sodium sulphate and concentrated under reduced pressure, and the residue was subjected to medium pressure, short column chromatography on silica gel, eluting with a mixture of ethyl acetate and hexane (1:2 v/v to give (E)-spiro{6-(3-oxooct-1-enyl)bicyclo[3,3,0]octane-2,2'-dioxolane} (128 mg), predominantly in the 6β-configuration.

REFERENCE EXAMPLE 17

A solution of (E)-spiro{6-(3-oxooct-1-enyl)bicyclo[3,3,0]octane-2,2'-dioxolane} (128 mg; prepared as described in Reference Example 16 and predominantly in the 6β-configuration) in dry tetrahydrofuran (0.5 ml) was added to a stirred solution of lithium tri-sec-butylborohydride in tetrahydrofuran (0.88 ml; 1M) at −78° C. under an argon atmosphere. The mixture was stirred at −78° C. for a further period of one hour and then at the ambient temperature for a period of 2 hours. The mixture was then cooled to 0° C. and treated with aqueous sodium hydroxide solution (0.67 ml; 3M), followed by aqueous hydrogen peroxide solution (0.33 ml; 30% w/v) and the mixture was stirred for a further period of 30 minutes at 0° C. The mixture was treated with water and sufficient sodium chloride to form a saturated solution, and then it was extracted with diethyl ether. The extracts were washed with saturated aqueous sodium chloride solution and dried over anhydrous sodium sulphate, and concentrated under reduced pressure. The resulting residue was subjected to medium pressure, short column chromatography on silica gel, eluting with a mixture of ethyl acetate and hexane (3:2 v/v), to give (E)-spiro{6-[(mixture of 3α and 3β)-hydroxyoct-1-enyl]bicyclo[3,3,0]octane-2,2'-dioxolane} (85 mg), predominantly in the 6β-configuration.

REFERENCE EXAMPLE 18

A mixture of (E)-spiro{6-[(mixture of 3α and 3β)-hydroxyoct-1-enyl]bicyclo[3,3,0]octane-2,2'-dioxolane} (85 mg; prepared as described in Reference Example 17 and predominantly in the 6β-configuration) and aqueous acetic acid solution (2.5 ml; 60% v/v) was left to stand at the ambient temperature for 16 hours. An excess of water was then added and the mixture was extracted with diethyl ether. The extract was washed with aqueous sodium carbonate solution (1M) and then with saturated aqueous sodium chloride solution, then it was dried over anhydrous sodium sulphate and concentrated under reduced pressure, to give (E)-2-[(mixture of 3α and 3β)-hydroxyoct-1-enyl]bicyclo[3,3,0]octan-6-one (67 mg), predominantly in the 2β-configuration.

REFERENCE EXAMPLE 19

A mixture of (E)-2-[(mixture of 3α and 3β)-hydroxyoct-1-enyl]-bicyclo[3,3,0]octan-6-one (67 mg; prepared as described in Reference Example 18 and predominantly in the 2β-configuration), tert-butyldimethylchlorosilane (60 mg), and imidazole (50 mg) in dimethylformamide (0.4 ml) was stirred at the ambient temperature for 3 hours. Water (5 ml) was then added and the mixture was extracted with diethyl ether. The extract was washed with saturated aqueous sodium chloride solution, dried over anhydrous sodium sulphate, and concentrated under reduced pressure, to give (E)-2-[(mixture of 3α and 3β)-tert-butyldimethylsilyloxyoct-1-enyl]bicyclo[3,3,0]octan-6-one (87 mg), predominantly in the 2β-configuration.

REFERENCE EXAMPLE 20

A solution of 6-acetoxy-2-carboxybicyclo[3,3,0]octane (3.2 g; prepared as described in Reference Example 5 and predominantly in the 2β-configuration) in tetrahydrofuran (30 ml) at −40° C. was treated with a solution of diborane in tetrahydrofuran (15 ml; 1M) under an argon atmosphere. The solution was stirred for 1 hour at −40° C. and then it was allowed to warm to 0° C. during 1 hour and was maintained at 0° C. for a further period of 150 minutes. The solution was then allowed to warm to 20° C. during 17 hours. The solution was then treated with aqueous ammonium chloride solution (10% w/v) and the mixture was concentrated in vacuo. The resulting residue was treated with ethyl acetate (100 ml) and washed with water (50 ml) and then with saturated aqueous sodium bicarbonate solution, and then was dried over anhydrous sodium sulphate. The solution was concentrated in vacuo to give an oil, which was subjected to medium pressure, short column chromatography on silica gel, eluting with a mixture of ethyl acetate and toluene (1:1 v/v), to give 6-acetoxy-2-hydroxymethylbicyclo[3,3,0]octane (2.8 g), predominantly in the 2β-configuration.

REFERENCE EXAMPLE 21

A stirred solution of 6-acetoxy-2-hydroxymethylbicyclo[3,3,0]octane (0.10 g; prepared as described in Reference Example 20 and predominantly in the 2β-configuration) in dry dichloromethane (2.5 ml) was treated with pyridinium chlorochromate (0.22 g) and anhydrous sodium bicarbonate (0.083 g). The resulting suspension was stirred for 150 minutes at the ambient temperature and was then placed directly onto a short column of silica gel and subjected to medium pressure, short column chromatography, eluting with a mixture of ethyl acetate and toluene (1:1 v/v) to give 6-acetoxy-2-formylbicyclo[3,3,0]octane (0.070 g), predominantly in the 2β-configuration.

REFERENCE EXAMPLE 22

A suspension of the sodium salt of dimethyl (2-oxoheptyl)phosphonate (0.105 g; prepared as described in Reference Example 55) in tetrahydrofuran (5.3 ml) at 0° C. was treated dropwise with a solution of 6-acetoxy-2-formylbicyclo[3,3,0]octane (70 mg; prepared as described in Reference Example 21 and predominantly in the 2β-configuration) in tetrahydrofuran (1.0 ml) with stirring. The resulting mixture was stirred for 18 hours at ambient temperature under an atmosphere of argon. The mixture was then treated dropwise with a solution of glacial acetic acid (200 mg) in diethyl ether (1 ml), and then the solution was concentrated in vacuo. The residue was treated with diethyl ether (20 ml) and water (20 ml) and the organic layer was separated. The aqueous layer was extracted with diethyl ether (3×20 ml). The combined extracts were washed with water and then with saturated aqueous sodium chloride solution, dried over magnesium sulphate and concentrated in vacuo, to give an oil which was subjected to chromatography on a silica gel column, to give (E)-6-acetoxy-2-(3-oxooct-1-enyl)bicyclo[3,3,0]octane (65.7 mg), predominantly in the 2β-configuration.

REFERENCE EXAMPLE 23

(E)-6-Acetoxy-2-(3-oxooct-1-enyl)bicyclo[3,3,0]octane (400 mg; prepared as described in Reference Example 22 and predominantly in the 2β-configuration) was dissolved in anhydrous tetrahydrofuran (10 ml) at −78° C. in an argon atmosphere with stirring and then it was treated with hexamethyl-phosphotriamide (400 mg) and then, dropwise, with a solution of potassium tri-sec-butylborohydride in tetrahydrofuran (1.5 ml; 1.0M). The solution was then allowed to warm to −30° C. during 3 hours and then the mixture was treated with a mixture of ethyl acetate (20 ml), water (50 ml) and hydrochloric acid (1 ml; 2N). The organic layer was removed and the aqueous layer was extracted with ethyl acetate (3×50 ml). The combined organic layers were washed with saturated aqueous sodium bicarbonate solution and then with saturated aqueous sodium chloride solution, dried over anhydrous sodium sulphate, and concentrated in vacuo. The resulting oil was subjected to medium pressure, short column chromatography on silica gel, eluting with mixtures of ethyl acetate and hexane of varying proportions (beginning at 1:9 v/v and ending at 1:1 v/v), to give (E)-6-acetoxy-2-[(mixture of 3α and 3β)-hydroxyoct-1-enyl]bicyclo[3,3,0]octane (390 mg), predominantly in the 2β-configuration.

REFERENCE EXAMPLE 24

(E)-6-Acetoxy-2-[(mixture of 3α and 3β)-hydroxyoct-1-enyl]bicyclo[3,3,0]octane (380 mg; prepared as described in Reference Example 23 and predominantly in the 2β-configuration) was dissolved in dry dimethylformamide (8 ml), with stirring, at 20° C. The solution was then treated with imidazole (330 mg) and tert-butyldimethylchlorosilane (420 mg) and stirred for 15 hours at 20° C. The reaction mixture was then treated with ethyl acetate (50 ml) and saturated aqueous sodium bicarbonate solution (50 ml). The organic layer was separated, washed with water (30 ml) and then with saturated aqueous sodium chloride solution, then dried over anhydrous sodium sulphate. Concentration in vacuo at 14 mmHg and then at 0.05 mmHg gave (E)-6-acetoxy-2-[(mixture of 3α and 3β)-tert-butyldimethylsilyloxyoct-1-enyl]bicyclo[3,3,0]octane (530 mg) in the form of an oil, which slowly solidified. It was predominantly in the 2β-configuration.

REFERENCE EXAMPLE 25

A solution of (E)-6-acetoxy-2-[(mixture of 3α and 3β)-tert-butyldimethylsilyloxyoct-1-enyl]bicyclo[3,3,0]octane (530 mg; prepared as described in Reference Example 24 and predominantly in the 2β-configuration) in methanol (10 ml) was treated with anhydrous potassium carbonate (193 mg). The mixture was heated at 40° C., with stirring, for 24 hours. The methanol was then removed in vacuo and the residue was extracted with dichloromethane (3×10 ml). Concentration of the extract in vacuo gave (E)-2-[(mixture of 3α and 3β)-tert-butyldimethylsilyloxyoct-1-enyl]-6-hydroxybicyclo[3,3,0]octane (430 mg), predominantly in the 2β-configuration.

REFERENCE EXAMPLE 26

A stirred solution of (E)-2-[(mixture of 3α and 3β)-tert-butyldimethylsilyloxyoct-1-enyl]-6-hydroxybicyclo[3,3,0]octane (430 mg prepared as described in Reference Example 25 and predominantly in the 2β-configuration) in dry dichloromethane (15 ml) was treated with potassium acetate (127 mg), potassium carbonate (110 mg) and pyridinium chlorochromate (561 mg), and the mixture was stirred for 150 minutes at 20° C. A further quantity of pyridinium chlorochromate (120 mg) was then added and the mixture was stirred for a further period of 1 hour. The mixture was then concentrated in vacuo and subjected to chromatography on a silica gel column, using a mixture of ethyl acetate and hexane (1:4 v/v) as eluant, to give (E)-2-[(mixture of 3α and 3β)-tertbutyldimethylsilyloxyoct-1-enyl]bicyclo[3,3,0]octan-6-one (330 mg), predominantly in the 2β-configuration.

REFERENCE EXAMPLE 27

(E)-2-[(mixture of 3α and 3β)-tert-Butyldimethylsilyloxyoct-1-enyl]bicyclo[3,3,0]octan-6-one (290 mg), prepared as described in Reference Example 19 or 26 and predominantly in the 2β-configuration, was dissolved, with stirring, in anhydrous diethyl ether (5 ml) at −78° C. in an argon atmosphere, and the solution was then treated with a freshly prepared solution of lithium diisopropylamide in diethyl ether (1.1 ml; 0.9M) at −78° C. and the mixture was stirred at −78° C. for 10 minutes. The mixture was then treated with 4-methoxycarbonylbutanal (208 mg) at −78° C. and stirred for a further period of 10 minutes. The reaction mixture was then treated with a solution of glacial acetic acid (100 mg) in diethyl ether (0.1 ml) at −78° C., and was then warmed to 20° C. The mixture was then diluted with ethyl acetate (25 ml), washed with aqueous ammonium chloride solution (2M) and then with saturated aqueous sodium chloride solution, dried over anhydrous sodium sulphate and concentrated in vacuo. The resulting oil (480 mg) was dissolved with stirring in dry benzene (5 ml) and then was treated with methanesulphonyl chloride (124 mg) and then, dropwise, with a solution of triethylamine (101 mg) in benzene (0.5 ml) at 20° C. The mixture was stirred for 1 hour at 20° C. and then was treated with 1,8-diazabicyclo[5,4,0]undec-7-ene (1.0 ml) and the resulting mixture was stirred for a further period of 1.5 hours at 20° C. The mixture was concentrated in vacuo to give a residue which was subjected to chromatography on a silica gel column using a mixture of hexane and ethyl acetate (1:9 v/v) as eluant, to give 6-[(E)-(mixture of 3α and 3β)-tert-butyldimethylsilyloxyoct-1-enyl]3-[(E)-4-methoxycarbonylbutylidene]-bicyclo[3,3,0]octan-2-one (92.4 mg), predominantly in the 6β-configuration, otherwise known as (±)-methyl (5E,13E)-(9S), [mixture of (15R) and (15S)]-6a-oxo-6,9-methano-15-tert-butyldimethylsilyloxy-prosta-5,13-dienoate.

REFERENCE EXAMPLE 28

(E)-2-[(mixture of 3α and 3β)-tert-Butyldimethylsilyloxyoct-1-enyl]bicyclo[3,3,0]octan-6-one (87 mg; prepared as described in Reference Example 19 or 26 and predominantly in the 2β-configuration), pyrrolidine (34 mg), cyclohexane (1 ml), and anhydrous magnesium sulphate (20 mg) were stirred together and heated at reflux under an argon atmosphere for 8 hours. After cooling, the mixture was filtered, and the magnesium sulphate residue was washed with a further quantity of cyclohexane. The combined filtrate and washing were concentrated under reduced pressure. The residue was stirred with 4-methoxycarbonylbutanal (38 mg) and anhydrous magnesium sulphate (20 mg) in toluene and in an argon atmosphere at 95° C. for 5 hours. The mixture was then cooled and filtered, and the filtrate was concentrated under reduced pressure. The resulting residue was stirred with a mixture of tetrahydrofuran and water (2 ml; 1:1 by volume) for 16 hours at room temperature. The mixture was then extracted with diethyl ether, and the combined ethereal extracts were washed with saturated aqueous sodium chloride solution, dried over anhydrous sodium sulphate, and concentrated under reduced pressure. The resulting residue was subjected to medium pressure, short column chromatography on silica gel, eluting with a mixture of ethyl acetate and hexane (1:4 v/v), to give 6-[(E)-(mixture of 3α and 3β)-tert-butyldimethylsilyloxyoct-1-enyl]-3-[(E)-4-methoxycarbonylbutylidene]bicyclo[3,3,0]octan-2-one (14.1 mg), predominantly in the 6β-configuration, otherwise known as (±)-methyl (5E,13E)-(9S), [mixture of (15R) and (15S)]-6a-oxo-6,9-methano-15-tert-butyldimethylsilyloxyprosta-5,13-dienoate [NMR in deuterochloroform: multiplets at 6.5, 5.4, 4.1 and 1.0–3.0 p.p.m., singlets at 3.7, 0.8 and 0.05 p.p.m.].

REFERENCE EXAMPLE 29

Dimethyl(2-cyclohexyl-2-oxoethyl)phosphonate (3.3 g) was added to a stirred suspension of sodium hydride (0.34 g) and 1,4,7,10,13,16-hexaoxacyclooctadecane (10 mg) in dry tetrahydrofuran (90 ml) in an atmosphere of argon and the mixture was stirred for 12 hours. The mixture was then cooled to 0° C. and treated dropwise with 6-acetoxy-2-formylbicyclo[3,3,0]octane (1.05 g; prepared as described in Reference Example 21 and predominantly in the 2β-configuration). The reaction mixture was allowed to warm to room temperature and then it was stirred for a further period of 24 hours. A solution of glacial acetic acid (400 mg) in diethyl ether (1 ml) was then added and the mixture was concentrated in vacuo. The residue was dissolved in ethyl acetate (10 ml) and the resulting solution was washed with water (10 ml) and then with saturated aqueous sodium chloride solution (10 ml), dried over magnesium sulphate, and concentrated in vacuo. The resulting oil was treated with acetic anhydride (1 ml) and pyridine (4 ml) at 20° C. and left to stand for 12 hours. Concentration at 0.01 mmHg gave an oil, which was subjected to chromatography on a silica gel column, eluting with mixtures of ethyl acetate and hexane (1:6 v/v and then 1:1 v/v), to give (E)-6-acetoxy-2-(3-cyclohexyl-3-oxoprop-1-enyl)bicyclo[3,3,0]octane (0.84 g), predominantly in the 2β-configuration.

REFERENCE EXAMPLE 30

A stirred solution of (E)-6-acetoxy-2-[(mixture of 3α and 3β)-cyclohexyl-3-oxoprop-1-enyl]bicyclo[3,3,0]octane (0.84 g; prepared as described in Reference Example 29 and predominantly in the 2β-configuration) in dry tetrahydrofuran (11.0 ml) and hexamethylphosphotriamide (2 ml) in an atmosphere of argon at −78° C. was treated, dropwise with stirring, with a solution of potassium tri-sec-butylborohydride in tetrahydrofuran (3.1 ml; 1.0M). The reaction mixture was then allowed to warm to 0° C. during 2 hours. The mixture was then treated with acetone (1 ml) and then with glacial acetic acid (1 ml) and stirred at 20° C. for 30 minutes. The mixture was then concentrated in vacuo. The residue was subjected to chromatography on a silica gel column, using a mixture of ethyl acetate and hexane (1:6 v/v) as eluant, to give (E)-6-acetoxy-2-[(mixture of 3α and 3β)-cyclohexyl-3-hydroxyprop-1-enyl]bicyclo[3,3,0]octane (0.32 g), predominantly in the 2β-configuration.

REFERENCE EXAMPLE 31

A stirred solution of (E)-6-acetoxy-2-[(mixture of 3α and 3β)-cyclohexyl-3-hydroxyprop-1-enyl]bicyclo[3,3,0]octane (0.32 g; prepared as described in Reference Example 30 and predominantly in the 2β-configuration) and imidazole (0.25 g), in dry dimethylformamide (10 ml) was treated with tert-butyldimethylchlorosilane (0.32 g) and left to stand at 20° C. for 60 hours. It was then diluted with water (50 ml) and extracted with ethyl acetate (4×20 ml). The combined organic extracts were washed with water (10 ml) and with saturated aqueous sodium chloride solution, dried over magnesium sulphate, and concentrated in vacuo at 0.01 mmHg to give (E)-6-acetoxy-2-[(mixture of 3α and 3β)-tert-butyldimethylsilyloxy-3-cyclcohexylprop-1-enyl]bicyclo[3,3,0]octane (0.40 g), predominantly in the 2β-configuration.

REFERENCE EXAMPLE 32

A mixture of (E)-6-acetoxy-2-[(mixture of 3α and 3β)-tert-butyldimethylsilyloxy-3-cyclohexylprop-1-enyl]bicyclo[3,3,0]octane (0.4 g; prepared as described in Example 31 and predominantly in the 2β-configuration), potassium carbonate (0.15 g) and methanol (10 ml) was heated at 50° C. for 8 hours. The mixture was then cooled and concentrated in vacuo. The resulting residue was extracted with dichloromethane (3×5 ml). Concentration in vacuo of the combined extracts gave (E)-2-[(mixture of 3α and 3β)-tert-butyldimethylsilyloxy-3-cyclohexylprop-1-enyl]-6-hydroxybicyclo[3,3,0]octane, predominantly in the 2β-configuration, in the form of an oil (0.36 g), sufficiently pure enough in the next stage.

REFERENCE EXAMPLE 33

A stirred solution of crude (E)-2-[(mixture of 3α and 3β)-tert-butyldimethylsilyloxy-3-cyclohexylprop-1-enyl]-6-hydroxybicyclo[3,3,0]octane (0.36 g; prepared as described in Reference Example 32 and predominantly in the 2β-configuration) in dichloromethane (15 ml) was treated with pyridinium chlorochromate (0.42 g) at 20° C. under an argon atmosphere and stirred for a further period of 3.5 hours. The mixture was then treated with silica gel (2 g) and carefully concentrated in vacuo. The resulting powder was placed onto a column of silica gel and eluted with a mixture of ethyl acetate and hexane (1:4 v/v), to give (E)-2-[(mixture of 3α and 3β)-tert-butyldimethylsilyloxy-3-cyclohexylprop-1-enyl]bicyclo[3,3,0]octan-6-one (0.22 g), predominantly in the 2β-configuration.

REFERENCE EXAMPLE 34

A stirred solution of (E)-2-[(mixture of 3α and 3β)-tert-butyldimethylsilyloxy-3-cyclohexylprop-1-enyl]-bicyclo[3,3,0]-octan-6-one (0.22 g; prepared as described in Reference Example 33 and predominantly in the 2β-configuration) in dry diethyl ether (3 ml) at −78° C. in an atmosphere of argon was treated with a solution of lithium diisopropylamide in diethyl ether (0.5 ml; 1.38M). The solution was stirred for 10 minutes at −78° C. and then treated with 4-methoxycarbonylbutanal (112 mg) at −78° C. After stirring for 10 minutes at −78° C. the reaction mixture was treated with a solution of glacial acetic acid (200 mg) in diethyl ether (400 mg) and the resulting white suspension was allowed to warm to room temperature. The mixture was then diluted with diethyl ether (20 ml) and poured into water (10 ml). The organic phase was separated and washed with aqueous sodium bicarbonate solution (5 ml; 10% w/v) and then with saturated aqueous sodium chloride solution, dried over magnesium sulphate and concentrated in vacuo. The resulting oil (0.4 g) was dissolved in benzene (0.2 ml) at 20° C. and treated with methanesulphonyl chloride (83 mg). The stirred mixture was then treated dropwise with triethylamine (0.095 ml) and stirred for a further period of 40 minutes in an argon atmosphere. The mixture was then treated with 1,8-diazabicyclo[5,4,0]undec-7-ene (0.51 g) and it was stirred for a further period of 2 hours. The mixture was then treated with diethyl ether (20 ml), glacial acetic acid (2 ml) and water (20 ml). The organic phase was separated and the aqueous layer was extracted with diethyl ether (2×10 ml). The combined organic solutions were washed with saturated aqueous sodium bicarbonate solution and then dried over anhydrous sodium sulphate. Concentration in vacuo, followed by chromatography on a silica gel column, using a mixture of ethyl acetate and hexane (1:9 v/v) as eluant, gave 6-[(E)-(mixture of 3α and 3β)-tert-butyldimethylsilyloxy-3-cyclohexylprop-1-enyl]-3-[(E)-4-methoxycarbonylbutylidene]bicyclo[3,3,0]octan-2-one (54 g), predominantly in the 6β-configuration, otherwise known as (±)-methyl (5E,13E)-(9S), [mixture of (15R) and (15S)]-6a-oxo-6,9-methano-15-tert-butyldimethylsilyloxy-15-cyclohexyl-16,17,18,19,20-pentanorprosta-5,13-dienoate.

REFERENCE EXAMPLE 35

(E)-2-(3-tert-Butyldimethylsilyloxy-3-cyclohexylprop-1-enyl)bicyclo[3,3,0]octan-6-one 65 mg; prepared as described in Reference Example 14, and in the form of (±)-(E)-2β-(3α-tert-butyldimethylsilyloxy-3-cyclohexylprop-1-enyl)bicyclo[3,3,0]octan-6-one was dissolved in dry tetrahydrofuran (2.63 ml). The solution was cooled to −70° C. under an atmosphere of argon and treated with a solution of lithium bis(trimethylsilyl)amide in tetrahydrofuran (1M; 0.212 ml), and the mixture was stirred at −70° C. for 10 minutes. The mixture was then treated with ethyl 4-oxocyclohexylcarboxylate (59 1 mg) and stirred for a further period of 3 hours at −70° C. The mixture was then treated with a solution of glacial acetic acid (0.02 ml) in diethyl ether (0.175 ml) and allowed to warm to ambient temperature. The mixture was then treated with water (20 ml) and extracted with ethyl acetate. The extract was washed with saturated aqueous sodium bicarbonate solution, and then with saturated aqueous sodium chloride solution, dried over anhydrous sodium sulphate, and concentrated under reduced pressure. The residual oil was subjected to medium pressure, short column chromatography on silica gel, using a mixture of ethyl acetate and hexane (1:3 v/v) as eluant, to give (E)-6-(3-tert-butyldimethylsilyloxy-3-cyclohexylprop-1-enyl)-3-(4-ethoxycarbonyl-1-hydroxycyclohex-1-yl)bicyclo[3,3,0]octan-2-one (33 mg), in the form of (±)-(E)-6β-(3α-tert-butyldimethylsilyloxy-3-cyclohexylprop-1-enyl)-3-(4-ethoxycarbonyl-1-hydroxycyclohex-1-yl)bicyclo[3,3,0]octan-2-one.

REFERENCE EXAMPLE 36

(E)-6-(3-tert-Butyldimethylsilyloxy-3-cyclohexylprop-1-enyl)-3-(4-ethoxycarbonyl-1-hydroxycyclohex-1-yl)bicyclo[3,3,0]octan-2-one {32 mg; prepared as described in Reference Example 35 and in the form of (±)-(E)-6β-(3α-tert-butyldimethylsilyloxy-3-cyclohexylprop-1-enyl)-3-(4-ethoxycarbonyl-1-hydroxycyclohex-1-yl)bicyclo[3,3,0]octan-2-one} was dissolved in benzene (0.234 ml) and treated with methanesulphonyl chloride (0.006 ml) with stirring at the ambient temperature and was then treated with triethylamine (0.010 ml) and stirred for 2 hours. The mixture was then treated with 1,8-diazabicyclo[5,4,0]undec-7-ene (0.055 ml) and the mixture was stirred for a further period of 150 minutes. The mixture was then treated with water (15 ml) and extracted with ethyl acetate. The ethyl acetate extract was washed with saturated aqueous sodium chloride solution, dried over anhydrous sodium sulphate, and concentrated under reduced pressure. The residue was subjected to medium pressure, short column chromatography on silica gel, using a mixture of ethyl acetate and hexane (1:8 v/v) as eluant, to give (E)-6-(3-tert-butyldimethylsilyloxy-3-cyclohexylprop-1-enyl)-3-(4-ethoxycarbonylcyclohexylidene)bicyclo[3,3,0]octan-2-one (15 mg), in the form of (±)-(E)-6β-(3α-tert-butyldimethylsilyloxy-3-cyclohexylprop-1-enyl)-3-(4-ethoxycarbonylcyclohexylidene)bicyclo[3,3,0]octan-2-one, otherwise known as (±)-ethyl(-13E)-(9S,15S)-6a-oxo-2,5-ethano-6,9-methano-15-tert-butyldimethylsilyloxy-15-cyclohexyl-16,17,18,19,20-pentanorprosta-5,13-dienoate.

REFERENCE EXAMPLE 37

By proceeding in a manner similar to that described in Reference Example 14, but replacing the starting material by the appropriate quantity of (E)-2-(3-cyclohexyl-3-hydroxyprop-1-enyl)bicyclo[3,3,0]octan-6-one, the less polar isomer prepared as described in Reference Example 13, in the form of (±)-(E)-2β-(3-cyclohexyl-3β-hydroxyprop-1-enyl)bicyclo[3,3,0]octan-6-one, there was prepared (E)-2-(3-tert-butyldimethylsilyloxy-3-cyclohexylprop-1-enyl)bicyclo[3,3,0]octan-6-one, in the form of (±)-(E)-2β-(3β-tert-butyldimethylsilyloxy-3-cyclohexylprop-1-enyl)bicyclo[3,3,0]octan-6-one.

REFERENCE EXAMPLE 38

By proceeding in a manner similar to that described in Reference Example 15, but replacing the starting material by the appropriate quantity of (E)-2-(3-tert-butyldimethylsilyloxy-3-cyclohexylprop-1-enyl)bicyclo[3,3,0]octan-6-one, prepared as described in Reference Example 37 and in the form of (±)-(E)-2β-(3β-tert-butyldimethylsilyloxy-3-cyclohexylprop-1-enyl)bicyclo[3,3,0]octan-6-one, there was prepared 6-[(E)-3-tert-butyldimethylsilyloxy-3-cyclohexylprop-1-enyl]-3-[(E)-4-methoxycarbonylbutylidene]bicyclo[3,3,0]octan-2-one, in the form of (±)-6β-[(E)-3β-tert-butyldimethylsilyloxy-3-cyclohexylprop-1-enyl]-3-[(E)-4-methoxycarbonylbutylidene]bicyclo[3,3,0]octan-2-one, otherwise known as (±)-methyl(5E,13E)-(9S,15R)-6a-oxo-6,9-methano-15-tert-butyldimethylsilyloxy-15-cyclohexyl-16,17,18,19,20-pentanorprosta-5,13-dienoate.

REFERENCE EXAMPLE 39

(E)-2-(3-tert-Butyldimethylsilyloxy-3-cyclohexylprop-1-enyl)bicyclo[3,3,0]octan-6-one, (65 mg), prepared as described in Reference Example 37 and in the form of (±)-(E)-2β-(3β-tert-butyldimethylsilyloxy-3-cyclohexylprop-1-enyl)bicyclo[3,3,0]octan-6-one was dissolved in dry tetrahydrofuran (2.63 ml). The solution was cooled to to −70° C. under an atmosphere of argon and treated with a solution of lithium bis(trimethylsilyl)amide in tetrahydrofuran (0.212 ml; 1M), and the mixture was stirred at −70° C. for 10 minutes. The mixture was then treated with ethyl 5-oxohexanoate (55 mg) and stirred for a further period of 5 hours at −70° C. The solution was treated with a solution of glacial acetic acid (0.02 ml) in diethyl ether (0.175 ml) and the mixture was allowed to warm to the ambient temperature. The mixture was then treated with water (20 ml) and extracted with ethyl acetate. The extract was washed with saturated aqueous sodium bicarbonate solution and then with saturated aqueous sodium chloride solution, dried over anhydrous sodium sulphate, and concentrated under reduced pressure. The residual oil was subjected to medium pressure, short column chromatography on silica gel, using a mixture of ethyl acetate and hexane (1:6 v/v) as eluant, to give 6-[(E)-3-tert-butyldimethylsilyloxy-3-cyclohexylprop-1-enyl]-3-(5-ethoxycarbonyl-2-hydroxypent-2-yl)bicyclo[3,3,0]octan-2-one (22 mg), in the form of 6β-[(E)-3β-tert-butyldimethylsilyloxy-3-cyclohexylprop-1-enyl]-3-(5-ethoxycarbonyl-2-hydroxypent-2-yl)bicyclo[3,3,0]octan-2-one, otherwise known as (±)-ethyl(13E)-(9S,15R)-6a-oxo-6,9-methano-15-tert-butyldimethylsilyloxy-15-cyclohexyl-5-hydroxy-5-methyl-16,17,18,19,20-pentanorprosta-13-dienoate.

REFERENCE EXAMPLE 40

A stirred solution of 6-[(E)-3-tert-butyldimethylsilyloxy-3-cyclohexylprop-1-enyl]-3-(5-ethoxycarbonyl-2-hydroxypent-2-yl)bicyclo[3,3,0]octan-2-one (26 mg), prepared as described in Reference Example 39 and in the form of 6β-[(E)-3β-tert-butyldimethylsilyloxy-3-cyclohexylprop-1-enyl]-3-(5-ethoxycarbonyl-2-hydroxypent-2-yl)bicyclo[3,3,0]octan-2-one, otherwise known as (±)-ethyl(13E)-(9S,15R)-6a-oxo-6,9-methano-15-tert-butyldimethylsilyloxy-15-cyclohexyl-5-hydroxy-5-methyl-16,17,18,19,20-pentanorprost-13- enoate, in benzene (0.19 ml) was treated with methanesulphonyl chloride (0.0048 ml) at the ambient temperature, followed by triethylamine (0.008 ml) and the mixture was stirred for 2 hours. It was then treated with 1,8-diazabicyclo[5,4,0]undec-7-ene (0.0446 ml) and the mixture was stirred for 2 hours. It was then treated with water (10 ml) and extracted with ethyl acetate. The extract was washed with saturated aqueous sodium chloride solution, dried over anhydrous sodium sulphate, and concentrated under reduced pressure. The resulting residue was subjected to medium pressure, short column chromatography on silica gel, using a mixture of ethyl acetate and hexane (1:8 v/v) as eluant, to give 6-[(E)-3-tert-butyldimethylsilyloxy-3-cyclohexylprop-1-enyl]-3-{[mixture of (E) and (Z)]-5-ethoxycarbonylpentylid-2-ene}bicyclo[3,3,0]octan-2-one (22 mg), in the form of (±)-6β-[(E)-3β-tert-butyldimethylsilyloxy-3-cyclohexylprop-1-enyl]-3-{[mixture of (E) and (Z)]-5-ethoxycarbonylpentylid-2-ene}bicyclo[3,3,-0]octan-2-one, otherwise known as (±)-ethyl [mixture of (5E and (5Z)],(13E)-(9S,15R)-6a-oxo-6,9-methano-5-methyl-15-tert-butyldimethylsilyloxy-15-cyclohexyl-16,17,18,19,20-pentanorprosta-5,13-dienoate.

REFERENCE EXAMPLE 41

By proceeding in a manner similar to that described in Reference Example 35, but replacing the starting material by the appropriate quantity of (E)-2-(3-tert-butyldimethylsilyloxy-3-cyclohexylprop-1-enyl)bicyclo[3,3,0]octan-6-one, prepared as described in Reference Example 37 and in the form of (±)-(E)-2β-(3β-tert-butyldimethylsilyloxy-3-cyclohexylprop-1-enyl)-bicyclo[3,3,0]octan-6-one, there was prepared (E)-6-(3-tert-butyldimethylsilyloxy-3-cyclohexylprop-1-enyl)-3-(4-ethoxycarbonyl-1-hydroxycyclohexyl)bicyclo[3,3,-0]octan-2-one, in the form of (±)-(E)-6β-(3β-tert-butyldimethylsilyloxy-3-cyclohexylprop-1-enyl)-3-(4-ethoxycarbonyl-1-hydroxycyclohex-1-yl)bicyclo[3,3,0]octan-2-one.

REFERENCE EXAMPLE 42

By proceeding in manner similar to that described in Reference Example 36, but replacing the starting material by the appropriate quantity of (E)-6-(3-tert-butyldimethylsilyloxy-3-cyclohexylprop-1-enyl)-3-(4-ethoxycarbonyl-1-hydroxycyclohex-1-yl)bicyclo[3,3,0]octan-2-one, prepared as described in Reference Example 41 and in the form of (±)-(E)-6β-(3β-tert-butyldimethylsilyloxy-3-cyclohexylprop-1-enyl)-3-(4-ethoxycarbonyl-1-hydroxycyclohex-1-yl)bicyclo[3,3,0]octan-2-one, there was prepared (E)-6-(3-tert-butyldimethylsilyloxy-3-cyclohexylprop-1-enyl)-3-(4-ethoxycarbonylcyclohexylidene)bicyclo[3,3,0]octan-2-one, in the form of (±)-(E)-6β-(3β-tert-butyldimethylsilyloxy-3-cyclohexylprop-1-enyl)-3-(4-ethoxycarbonylcyclohexylidene)bicyclo[3,3,0]octan-2-one, otherwise known as (±)-ethyl (13E)-(9S,15R)-6a-oxo-2,5-ethano-6,9-methano-15-tert-butyldimethylsilyloxy-15-cyclohexyl-16,17,18,19,20-pentanorprosta-5,13-dienoate.

REFERENCE EXAMPLE 43

A mixture of the lithium salt of dimethyl (2-oxo-3-phenoxypropyl)phosphonate (0.25 g), spiro{6-formylbicyclo[3,3,0]octane-2,2'-dioxolane} (0.15 g), prepared as described in Reference Example 10 and predominantly in the 6β-configuration, and tetrahydrofuran (9 ml) was stirred for 16 hours at room temperature. The mixture was then concentrated under reduced pressure, and then treated with water and diethyl ether. The layers were separated, and the aqueous layer was extracted with a further quantity of diethyl ether. The combined extracts were washed with saturated aqueous sodium chloride solution, dried over anhydrous sodium sulphate, and concentrated under reduced pressure. The resulting residue was subjected to medium pressure, short column chromatography on silica gel, using a mixture of ethyl acetate and hexane (2:3 v/v) as eluant, to give (E)-spiro{6-(3-oxo-4-phenoxybut-1-enyl)-bicyclo[3,3,0]octan-2,2'-dioxolane} (0.16 g), predominantly in the 6β-configuration.

REFERENCE EXAMPLE 44

A stirred solution of lithium tri-sec-butylborohydride in tetrahydrofuran (1.24 ml; 1M), was treated with a solution of (E)-spiro{6-(3-oxo-4-phenoxybut-1-enyl)-bicyclo[3,3,0]octan-2,2'-dioxolane} (0.20 g; prepared as described in Reference Example 43 and predominantly in the 6β-configuration) in dry tetrahydrofuran (0.7 ml) at −78° C. under an atmosphere of argon. The mixture was stirred at −78° C. for one hour and then at the ambient temperature for 2 hours. It was then treated with aqueous sodium hydroxide solution (1.24 ml; 3M) at 0° C., followed by aqueous hydrogen peroxide solution (0.62 ml; 30% w/v) and the mixture was stirred for a further period of 30 minutes at 0° C. The mixture was treated with water and sufficient sodium chloride to form a saturated solution, and then it was extracted with diethyl ether. The extract was washed with saturated sodium chloride solution, dried over anhydrous sodium sulphate, and concentrated under reduced pressure, to give (E)-spiro{6-(3-hydroxy-4-phenoxybut-1-enyl)bicyclo[3,3,0]octan-2,2'-dioxolane} (0.22 g), predominantly in the 6β-configuration, and sufficiently pure for use in the next stage.

REFERENCE EXAMPLE 45

A mixture of (E)-spiro{6-(3-hydroxy-4-phenoxybut-1-enyl)bicyclo[3,3,0]octan-2,2'-dioxolane} (0.22 g; prepared as described in Reference Example 44 and predominantly in the 6β-configuration) and aqueous acetic acid (6 ml; 60% w/v) was left to stand at the ambient temperature for 16 hours. The mixture was then treated with an excess of water and extracted with diethyl ether. The extract was washed with aqueous sodium carbonate solution (1M), and then with saturated aqueous sodium chloride solution, dried over anhydrous sodium sulphate, and concentrated under reduced pressure, to give (E)-2-(3-hydroxy-4-phenoxybut-1-enyl)-bicyclo[3,3,0]octan-6-one (0.16 g), predominantly in the 2β-configuration. This material was purified and separated into two epimeric pairs of enantiomers by short column chromatography on silica gel, eluting with a mixture of ethyl acetate and hexane (1:2 v/v). The less polar component (49 mg) was (±)-(E)-2β-(3β-hydroxy-4-phenoxybut-1-enyl)bicyclo[3,3,0]octan-6-one and the more polar component (27 mg) was (±)-(E)-2β-(3α-hydroxy-4-phenoxybut-1-enyl)bicyclo[3,3,0]octan-6-one. A mixture of these components (43 mg), that is to say (3S)-(E)-2β-[(mixture of 3α and 3β)-hydroxy-4-phenoxybut-1-enyl]bicyclo[3,3,0]octan-6-one, was also obtained from the column.

REFERENCE EXAMPLE 46

A mixture of (E)-2-(3-hydroxy-4-phenoxybut-1-enyl)-bicyclo[3,3,0]octan-6-one (49 mg), the less polar component prepared as described in Reference Example 45 and in the form of (±)-(E)-2β-(3β-hydroxy-4-phenoxybut-1-enyl)bicyclo[3,3,0]octan-6-one, tert-butyldimethylchlorosilane (31 mg), and imidazole (29 mg) in dimethylformamide (0.116 ml) was stirred at the ambient temperature for 2 hours. The mixture was then treated with water (10 ml) and extracted with diethyl ether. The extract was washed with saturated aqueous sodium chloride solution, dried over anhydrous sodium sulphate and concentrated under reduced pressure, to give (E)-2-(3-tert-butyldimethylsilyloxy-4-phenoxybut-1-enyl)bicyclo[3,3,0]octan-6-one (76 mg), in the form of (±)-(E)-2β-(3β-tert-butyldimethylsilyloxy-4-phenoxybut-1-enyl)bicyclo[3,3,0]octan-6-one.

REFERENCE EXAMPLE 47

A stirred solution of (E)-2-(3-tert-butyldimethylsilyloxy-4-phenoxybut-1-enyl)bicyclo[3,3,0]octan-6-one (75 mg), prepared as described in Reference Example 46 and in the form of (±)-(E)-2β-(3β-tert-butyldimethylsilyloxy-4-phenoxybut-1-enyl)bicyclo[3,3,0]octan-6-one, in dry tetrahydrofuran (2.55 ml) was cooled to −70° C. under an atmosphere of argon and treated with a solution of lithium bis(trimethylsilyl)amide in tetrahydrofuran (1M; 0.204 ml), and the mixture was stirred at −70° C. for 10 minutes. The mixture was then treated with 4-methoxycarbonylbutanal (44 mg) and stirred for a further period of 150 minutes at −70° C. The mixture was then treated with a solution of glacial acetic acid (0.019 ml) in diethyl ether (0.17 ml) and allowed to warm to the ambient temperature. The mixture was treated with water (25 ml) and extracted with ethyl acetate. The extract was washed with saturated aqueous sodium bicarbonate solution, and with saturated aqueous sodium chloride solution, dried over anhydrous sodium sulphate, and concentrated under reduced pressure. The residual oil was subjected to medium pressure, short column chromatography on silica gel, eluting with a mixture of ethyl acetate and hexane (1:2 v/v), to give 6-[(E)-3-tert-butyldimethylsilyloxy-4-phenoxybut-1-enyl]-3-(1-hydroxy-4-methoxycarbonylbut-1-yl)bicyclo[3,3,0]octan-2-one (47 mg), in the form of (±)-6β-[(E)-3β-tert-butyldimethylsilyloxy-4-phenoxybut-1-enyl]-3-(1-hydroxy-4-methoxycarbonylbut-1-yl)bicyclo[3,3,0]octan-2-one.

REFERENCE EXAMPLE 48

A stirred solution of 6-[(E)-3-tert-butyldimethylsilyloxy-4-phenoxybut-1-enyl]-3-(1-hydroxy-4-methoxycarbonylbut-1-yl)bicyclo[3,3,0]octan-2-one (38 mg), prepared as described in Reference Example 47 and in the form of (±)-6β-[(E)-3β-tert-butyldimethylsilyloxy-4-phenoxybut-1-enyl]-3-(1-hydroxy-4-methoxycarbonylbut-1-yl)bicyclo[3,3,0]octan-2-one, in dry benzene (0.28 ml) was treated with methanesulphonyl chloride (0.0072 ml) at the ambient temperature and then with triethylamine (0.012 ml) and stirred for 2 hours. It was then treated with 1,8-diazabicyclo[5,4,0]undec-7-ene (65 mg) and stirred for 150 minutes. The mixture was treated with water (15 ml) and extracted with ethyl acetate. The extract was washed with saturated aqueous sodium chloride solution, dried over anhydrous sodium sulphate, and concentrated under reduced pressure. The resulting residue was then subjected to medium pressure, short column chromatography on silica gel, eluting with a mixture of ethyl acetate and hexane (23:77 v/v), to give 6-[(E)-3-tert-butyldimethylsilyloxy-4-phenoxybut-1-enyl]-3-[(E)-4-methoxycarbonylbutylidene]bicyclo[3,3,0]octan-2-one (24 mg), in the form of (±)-6β-[(E)-3β-tert-butyldimethylsilyloxy-4-phenoxybut-1-enyl]-3-[(E)-4-methoxycarbonylbutylidene]bicyclo[3,3,0]octan-2-one, otherwise known as (±)-methyl (5E,13E)-(9S,15S)-6a-oxo-6,9-methano-15-tert-butyldimethylsilyloxy-16-phenoxy-17,18,19,20-tetranorprosta-5,13-dienoate.

REFERENCE EXAMPLE 49

By proceeding in a manner similar to that described in Reference Example 46, but replacing the starting material by the appropriate quantity of (E)-2-(3-hydroxy-4-phenoxybut-1-enyl)bicyclo[3,3,0]octan-6-one, the more polar component prepared as described in Reference Example 45, and in the form of (±)-(E)-2β-(3α-hydroxy-4-phenoxybut-1-enyl)bicyclo[3,3,0]octan-6-one, there was prepared (E)-2-(3-tert-butyldimethylsilyloxy-4-phenoxybut-1-enyl)bicyclo[3,3,0]-6-one, in the form of (±)-(E)-2β-(3α-tert-butyldimethylsilyloxy-4-phenoxybut-1-enyl)bicyclo[3,3,0]octan-6-one.

REFERENCE EXAMPLE 50

By proceeding in a manner similar to that described in Reference Example 47, but replacing the starting material by the appropriate quantity of (E)-2-(3-tert-butyldimethylsilyloxy-4-phenoxybut-1-enyl)bicyclo[3,3,0]octan-6-one, prepared as described in Reference Example 49, and in the form of (±)-(E)-2β-(3α-tert-butyldimethylsilyloxy-4-phenoxybut-1-enyl)bicyclo[3,3,0]octan-2-one, there was prepared 6-[(E)-3-tert-butyldimethylsilyloxy-4-phenoxybut-1-enyl]-3-(1-hydroxy-4-methoxycarbonylbut-1-yl)bicyclo[3,3,0]octan-2-one, in the form of (±)-6β-[(E)-3α-tert-butyldimethylsilyloxy-4-phenoxybut-1-enyl]-3-(1-hydroxy-4-methoxycarbonylbut-1-yl)bicyclo[3,3,0]octan-2-one.

REFERENCE EXAMPLE 51

By proceeding in a manner similar to that described in Reference Example 48, but replacing the starting material by the appropriate quantity of 6-[(E)-3-tert-butyldimethylsilyloxy-4-phenoxybut-1-enyl]-3-(1-hydroxy-4-methoxycarbonylbut-1-yl)bicyclo[3,3,0]octan-2-one, prepared as described in Reference Example 50, and in the form of (±)-6β-[(E)-3α-tert-butyldimethylsilyloxy-4-phenoxybut-1-enyl]-3-(1-hydroxy-4-methoxycarbonylbut-1-yl)bicyclo[3,3,0]octan-2-one, there was prepared 6-[(E)-3-tert-butyldimethylsilyloxy-4-phenoxybut-1-enyl]-3-[(E)-4-methoxycarbonylbutylidene]bicyclo[3,3,0]octan-2-one, in the form of (±)-6β-[(E)-3α-tert-butyldimethylsilyloxy-4-phenoxybut-1-enyl]-3-[(E)-4-methoxycarbonylbutylidene]bicyclo[3,3,0]octan-2-one, otherwise known as (±)-methyl (5E,13E)-(9S,15R)-6a-oxo-6,9-methano-15-tert-butyldimethylsilyloxy-16-phenoxy-17,18,19,20-tetranorprosta-5,13-dienoate.

REFERENCE EXAMPLE 52

By proceeding in a manner similar to that described in Reference Example 46, but replacing the starting material by the appropriate quantity of (E)-2-(3-hydroxy-4-phenoxybut-1-enyl)bicyclo[3,3,0]octan-6-one, the mixture of components prepared as described in Reference Example 45 and in the form of (±)-(E)-2β-[(mixture of 3α and 3β)-hydroxy-4-phenoxybut-1-enyl]bicyclo[3,3,0]octan-6-one, there was prepared (E)-2-(3-tert-butyldimethylsilyloxy-4-phenoxybut-1-enyl)bicyclo[3,3,0]octan-6-one, in the form of (±)-(E)-2β-[(mixture of 3α and 3β)-tert-butyldimethylsilyloxy-4-phenoxybut-1-enyl]bicyclo[3,3,0]octan-6-one.

REFERENCE EXAMPLE 53

By proceeding in a manner to that described in Reference Example 47, but replacing the starting material by the appropriate quantity of (E)-2-(3-tert-butyldimethylsilyloxy-4-phenoxybut-1-enyl)bicyclo[3,3,0]octan-6-one, prepared as described in Reference Example 52, and in the form of (±)-(E)-2β-[(mixture of 3α and 3β)-tert-butyldimethylsilyloxy-4-phenoxybut-1-enyl]bicyclo[3,3,0]octan-6-one, there was prepared 6-(E)-3-tert-butyldimethylsilyloxy-4-phenoxybut-1-enyl-3-(1-hydroxy-4-methoxycarbonylbut-1-yl)-bicyclo[3,3,0]octan-2-one, in the form of (±)-6β-[(E)-(mixture of 3α and 3β)-tert-butyldimethylsilyloxy-4-phenoxybut-1-enyl]-3-(1-hydroxy-4-methoxycarbonylbut-1-yl)bicyclo[3,3,0]octan-2-one.

REFERENCE EXAMPLE 54

By proceeding in a manner similar to that described in Reference Example 48, but replacing the starting material by the appropriate quantity of 6-[(E)-3-tert-butyldimethylsilyloxy-4-phenoxybut-1-enyl]-3-(1-hydroxy-4-methoxycarbonylbut-1-yl)bicyclo[3,3,0]octan-2-one, prepared as described in Reference Example 53, and in the form of (±)-6β-[(E)-(mixture of 3α and 3β)-tert-butyldimethylsilyloxy-4-phenoxybut-1-enyl]-3-(1-hydroxy-methoxycarbonylbut-1-yl)bicyclo[3,3,0]octan-2-one, there was prepared 6-[(E)-3-tert-butyldimethylsilyloxy-4-phenoxybut-1-enyl]-3-[(E)-4-methoxycarbonylbutylidene]bicyclo[3,3,0]octan-2-one, in the form of (±)-6β-[(E)-(mixture of 3α and 3β)-tert-butyldimethylsilyloxy-4-phenoxybut-1-enyl]-3-[(E)-4-methoxycarbonylbutylidene]bicyclo[3,3,0]octan-2-one, otherwise known as (±)-methyl (5E,13E)-(9S), [mixture of (15R) and (15S)]-6a-oxo-6,9-methano-15-tert-butyldimethylsilyloxy-16-phenoxy-17,18,19,20-tetranorprosta-5,13-dienoate.

REFERENCE EXAMPLE 55

A suspension of sodium hydride in mineral oil (50% w/w; 96 mg) was mixed with tetrahydrofuran (15 ml) and treated with dimethyl(2-oxoheptyl)phosphonate (0.48 g), dropwise, at 0° C. under an atmosphere of argon. After 90 minutes the precipitated solid was filtered off under an atmosphere of nitrogen, washed with tetrahydrofuran (2×5 ml) and dried in vacuo at 20° C./0.01 mmHg, to give the sodium salt of dimethyl (2-oxoheptyl)phosphonate (180 mg), m.p. 130°-132° C. [Elemental analysis: C,44.2;H,7.4;P,12.4%; calculated: C,44.2;H,7.4;P,12.7%].

The present invention includes within its scope pharmaceutical compositions which comprise at least one compound of the general formula shown in FIG. II or, when $R^1$ represents a hydrogen atom, a non-toxic salt thereof, or a cyclodextrin clathrate thereof, together with a pharmaceutical carrier or coating. In clinical practice the compounds of the formula shown in FIG. II will normally be administered orally, rectally, vaginally or parenterally.

Methods of presentation of pharmaceutically active compounds are well known in the art and a suitable vehicle may be determined by the physician, pharmacist or veterinarian, depending upon such factors as the effect sought, the size, age, sex and condition of the patient and, for veterinary uses, the species of the animal to be treated, and on the physical properties of the active compound. The compositions may also contain, as is usual in the art, such materials as solid or liquid diluents, wetting agents, preservatives, flavouring and colouring agents and the like.

Solid compositions for oral administration include compressed tablets, pills, dispersible powders, and granules. In such solid compositions one or more of the active compounds is, or are, admixed with at least one inert diluent such as calcium carbonate, potato starch, alginic acid, or lactose. The compositions may also comprise, as is normal practice, additional substances other than inert diluents, e.g. lubricating agents, such as magnesium stearate. Liquid compositions for oral administration include pharmaceutically-acceptable emulsions, solutions, suspensions, syrups and elixirs containing inert diluents commonly used in the art, such as water and liquid paraffin. Besides inert diluents such compositions may also comprise adjuvants, such as wetting and suspending agents, and sweetening, flavouring, perfuming and preserving agents. The compositions according to the invention, for oral administration, also include capsules of absorbable material such as gelatin containing one or more of the active substances with or without the addition of diluents or excipients.

Solid compositions for vaginal administration include pessaries formulated in manner known per se and containing one or more of the active compounds.

Solid compositions for rectal administration include suppositories formulated in manner known per se and containing one or more of the active compounds.

Preparations according to the invention for parenteral administration include sterile aqueous or non-aqueous solutions, suspensions, or emulsions, Examples of non-aqueous solvents or suspending media are propylene glycol, polyethylene glycol, vegetable oils such as olive oil, and injectable organic esters such as ethyl oleate. These compositions may also include adjuvants such as preserving, wetting, emulsifying and dispersing agents. They may be sterilised, for example, by filtration through a bacteria-retaining filter, by incorporation of sterilising agents in the composition, by irradiation, or by heating. They may also be manufactured in the form of sterile solid compositions, which can be dissolved in sterile water or some other sterile injectable medium immediately before use.

The compounds of the formula shown in FIG. II may alternatively be administered orally by any method known per se for administration by inhalation of drugs which are not themselves gaseous under normal conditions of administration. Thus, a solution of the active ingredient in a suitable pharmaceutically-acceptable solvent, for example water, can be nebulized by a mechanical nebulizer, for example a Wright Nebulizer, to give an aerosol of finely-divided liquid particles suitable for inhalation. The active ingredients may also be administered orally by inhalation in the form of aerosols generated from self-propelling pharmaceutical compositions.

The percentage of active ingredient in the compositions of the invention may be varied, it being necessary that it should constitute a proportion such that a suitable dosage for the therapeutic effect desired shall be obtained. Obviously several unit dosage forms may be administered at about the same time. In general, the preparations should normally contain at least 0.025% by weight of active subtance when required for administration by injection; for oral administration the preparations will normally contain at least 0.1% by weight of active substance. The dose employed depends upon the desired therapeutic effect, the route of administration and the duration of the treatment. In the adult, the doses are generally between 0.0002 and 2.0 mg/kg body weight. If necessary these doses may be repeated as and when required.

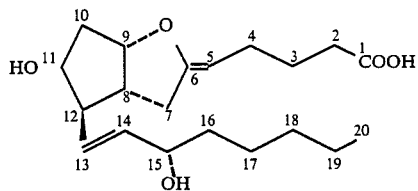

FIG. I

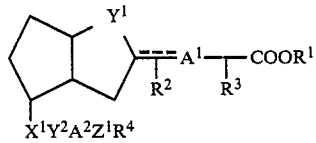

FIG. II

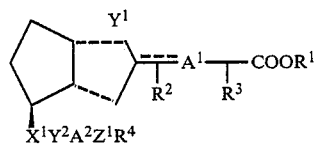

FIG. III

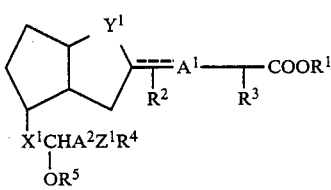

FIG. IV

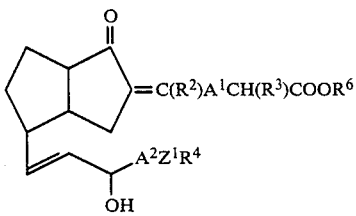

FIG. V

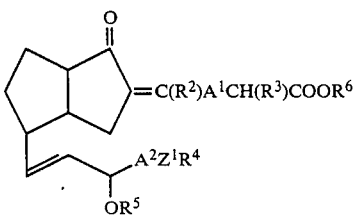

FIG. VI

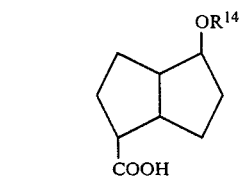

FIG. XII

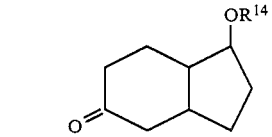

FIG. XIII

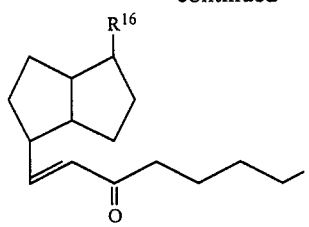

FIG. XV

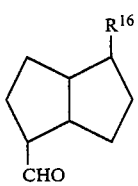

FIG. XVI

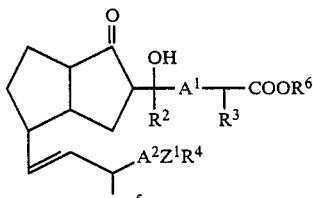

FIG. XVIII

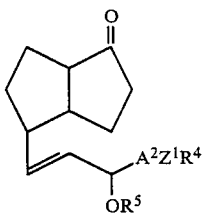

FIG. XIX

We claim:

1. A prostaglandin analogue of the formula:

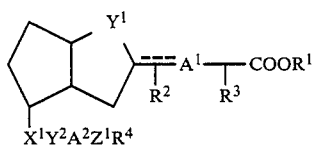

II (wherein $R^1$ represents a hydrogen atom or a straight- or branched-chain alkyl group of 1 to 6 carbon atoms, $Y^1$ represents a carbonyl or hydroxymethylene group, ==== represents a single or double bond, $A^1$ represents an alkylene linkage containing 2 or 3 carbon atoms and optionally bearing a methyl or ethyl substituent, $R^2$ represents a hydrogen atom or a methyl or ethyl group and $R^3$ represents a hydrogen atom or else $R^2$ and $R^3$ form an alkylene linkage containing 2 or 3 carbon atoms, optionally bearing a methyl or ethyl substituent, such that the symbols $A^1$, $R^2$ and $R^3$, together with the carbon atoms through which they are connected, form a cycloalkyl ring of 6, 7 or 8 carbon atoms, optionally bearing one or two methyl or ethyl substituents, $X^1$ represents an ethylene or trans-vinylene group, $Y^2$ represents a carbonyl or hydroxymethylene group, and either (i) $A^2$ represents a straight- or branched-alkylene chain containing from 1 to 3 carbon atoms, $Z^1$ represents a direct bond or an oxygen or sulphur atom, and $R^4$ represents a straight- or branched-chain alkyl group containing from 1 to 12 carbon atoms, optionally substituted by a cycloalkyl group containing from 3 to 8 carbon atoms, or represents a cycloalkyl group containing from 3 to 8 carbon atoms, or represents a phenyl group optionally substituted by a halogen atom or by a trifluoromethyl group or by a straight- or branched-chain alkyl or alkoxy group containing from 1 to 6 carbon atoms, or (ii) $A^2$ and $Z^1$ both represent direct bonds and $R^4$ represents a straight- or branched-chain alkyl group containing from 1 to 12 carbon atoms, optionally substituted by a cycloalkyl group containing from 3 to 8 carbon atoms, or represents a cycloalkyl group containing from 3 to 8 carbon atoms) or a cyclodextrin clathrate thereof or, when $R^1$ represents a hydrogen atom, a non-toxic salt thereof.

2. A prostaglandin analogue according to claim 1 wherein the hydrogen atoms attached to the 8- and 9-positions are both in beta configuration.

3. A prostaglandin analogue according to claim 1 wherein the sidechain attached to the 12-position is cis with respect to the hydrogen atoms attached to the 8- and 9-positions.

4. A prostaglandin analogue according to claim 1 conforming to the formula:

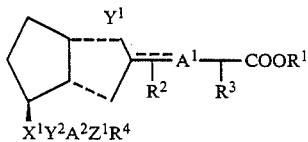

(wherein $A^1$, $A^2$, $R^1$, $R^2$, $R^3$, $R^4$, ====, $X^1$, $Y^1$, $Y^2$ and $Z^1$ are as hereinbefore defined) and its enantiomers, or a non-toxic salt or cyclodextrin clathrate thereof.

5. A prostaglandin analogue according to claim 1 wherein $A^1$ represents an ethylene group.

6. A prostaglandin analogue according to claim 1 wherein $A^2$ represents a direct bond or a methylene group.

7. A prostaglandin analogue according to claim 1 wherein $R^4$ represents a straight- or branched-chain alkyl group containing from 1 to 12 carbon atoms or represents a cycloalkyl group containing from 3 to 8 carbon atoms or a phenyl group.

8. A prostaglandin analogue according to claim 7 wherein the straight- or branched-chain alkyl group contains from 4 to 8 carbon atoms.

9. A prostaglandin analogue according to claim 7 wherein the straight- or branched-chain alkyl group is pentyl and the cycloalkyl group is cyclohexyl.

10. A prostaglandin analogue according to claim 1 wherein $R^1$ represents a hydrogen atom or a methyl or ethyl group.

11. A prostaglandin analogue according to claim 1 wherein $R^2$ represents a hydrogen atom or a methyl group.

12. A prostaglandin analogue according to claim 1 wherein $R^3$ represents a hydrogen atom.

13. A prostaglandin analogue according to claim 1 wherein $A^1$, $R^2$ and $R^3$, together with the carbon atoms through which they are connected, form a cyclohexyl ring.

14. A prostaglandin analogue according to claim 1 wherein ==== represents a vinylene group.

15. A prostaglandin analogue according to claim 1 wherein $X^1$ represents a trans-vinylene group.

16. A prostaglandin analogue according to claim 1 wherein $Y^2$ represents a hydroxymethylene group.

17. A prostaglandin analogue according to claim 1 wherein $Z^1$ represents a direct bond or an oxygen atom.

18. A compound according to claim 1 which is (±)-methyl (5E,13E)-(9S,15S)-6a-oxo-6,9-methano-15-cyclohexyl-15-hydroxy-16,17,18,19,20-pentanorprosta-5,13-dienoate, (±)-(5E,13E)-(9S,15S)-6a-oxo-6,9-methano-15-cyclohexyl-15-hydroxy-16,17,18,19,20-pentanorprosta-5,13-dienoic acid, (±)-[mixture of (5E) and (5Z), (13E)-(9S,15S)-6-a-oxo-6,9-methano-15-cyclohexyl-15-hydroxy-16,17-18,19,20-pentanorprosta-5,13-dienoic acid, (±)-methyl (5E,13E)-(9S), [mixture of (15R) and (15S)]-6a-oxo-6,9-methano-15-hydroxyprosta-5,13-dienoate, (±)-(5E,13E)-(9S), [mixture of (15R) and (15S]-6-a-oxo-6,9-methano-15-hydroxyprosta-5,13-dienoic acid, (±)-(5Z,13E)-(9S), [mixture of (15R) and (15S)]-6a-oxo-6,9-methano-15-hydroxyprosta-5,13-dienoic acid, (±)-methyl (5Z,13E)-(9S), [mixture of (15R) and (15S)]-6a-oxo-6,9-methano-15-hydroxyprosta-5,13-dienoate, (±)-methyl (5E,13E)-(9S), [mixture of (15R) and (15S)]-6a-oxo-6,9-methano-15-cyclohexyl-15-hydroxy-16,17,18,19,20-pentanorprosta-5,13-dienoate, (±)-(5E,13E)-(9S), [mixture of (15R) and (15S)]-6a-oxo-6,9-methano-15-cyclohexyl-15-hydroxy-16,17,18,19,20-pentanorprosta-5,13-dienoic acid, or (±)-(5E,13E)-(6aS,9S), [mixture of (15R) and (15S)]-6a,15-dihydroxy-6,9-methano-15-cyclohexyl-16,17,18,19,20-pentanorprosta-5,13-dienoic acid.

19. A compound according to claim 1 which is (±)-ethyl (13E)-(9S,15S)-6a-oxo-2,5-ethano-6,9-methano-15-hydroxy-15-cyclohexyl-16,17,18,19,20-pentanorprosta-5,13-dienoate, (±)-methyl (5E,13E)-(9S,15R)-6a-oxo-6,9-methano-15-cyclohexyl-15-hydroxy-16,17,18,19,20-pentanorprosta-5,13-dienoate, (±)-(5E,13E)-(9S,15R)-6a-oxo-6,9-methano-15-cyclohexyl-15-hydroxy-16,17,18,19,20-pentanorprosta-5,13-dienoic acid, (±)-ethyl [mixture of (5E) and (5Z)], (13E)-(9S,15R)-6a-oxo-6,9-methano-5-methyl-15-cyclohexyl-15-hydroxy-16,17,18,19,20-pentanorprosta-5,13-dienoate, (±)-ethyl (13E)-(9S,15R)-6a-oxo-2,5-ethano-6,9-methano-15-hydroxy-15-cyclohexyl-16,17,18,19,20-pentanorprosta-5,13-dienoate, (±)-methyl (5E,13E)-(9S,15S)-6-a-oxo-6,9-methano-15-hydroxy-16-phenoxy-17,18,19,20-tetranorprosta-5,13-dienoate, (±)-methyl (5E,13E)-(9S,15R)-6a-oxo-6,9-methano-15-hydroxy-16-phenoxy-17,18,19,20-tetranorprosta-5,13-dienoate, or (±)-methyl (5E,13E)-(9S), [mixture of (15R) and (15S)]-6a-oxo-6,9-methano-15-hydroxy-16-phenoxy-17,18,19,20-tetranorprosta-5,13-dienoate.

20. A pharmaceutical composition useful in the treatment of hypertension and thrombosis which comprises, as active ingredient, an effective amount of a prostaglandin analogue according to claim 1, or a non-toxic salt or cyclodextrin clathrate thereof, in association with a pharmaceutical carrier or coating.

21. A method for the treatment of a patient suffering from, or subject to, hypertension or thrombosis which comprises administering to the patient an effective amount of a prostaglandin analogue according to claim 1, or a non-toxic salt thereof or a cyclodextrin clathrate thereof.

* * * * *